(12) United States Patent
Delcourt

(10) Patent No.: US 9,903,873 B2
(45) Date of Patent: Feb. 27, 2018

(54) METHOD FOR SELECTING STABLE PROTEINS IN NON-STANDARD PHYSICOCHEMICAL CONDITIONS

(75) Inventor: Marc Delcourt, Paris (FR)

(73) Assignee: BIOMETHODES, Evry (FR)

( * ) Notice: Subject to any disclaimer, the term of this patent is extended or adjusted under 35 U.S.C. 154(b) by 1452 days.

(21) Appl. No.: 11/916,112

(22) PCT Filed: Apr. 4, 2006

(86) PCT No.: PCT/FR2006/000735
§ 371 (c)(1),
(2), (4) Date: Nov. 30, 2007

(87) PCT Pub. No.: WO2006/134240
PCT Pub. Date: Dec. 21, 2006

(65) Prior Publication Data
US 2009/0131264 A1 May 21, 2009

(30) Foreign Application Priority Data

Jun. 10, 2005 (FR) .................................. 05 05935

(51) Int. Cl.
| | |
|---|---|
| C40B 30/00 | (2006.01) |
| C40B 30/06 | (2006.01) |
| C12N 15/62 | (2006.01) |
| C12N 15/63 | (2006.01) |
| G01N 33/68 | (2006.01) |
| C12N 15/52 | (2006.01) |

(52) U.S. Cl.
CPC ......... *G01N 33/6842* (2013.01); *C12N 15/62* (2013.01); *C12N 15/63* (2013.01); *C40B 30/00* (2013.01); *C40B 30/06* (2013.01); *G01N 33/68* (2013.01); *C07K 2319/00* (2013.01); *C12N 15/52* (2013.01)

(58) Field of Classification Search
None
See application file for complete search history.

(56) References Cited

U.S. PATENT DOCUMENTS

| | | |
|---|---|---|
| 6,448,087 B1 | 9/2002 | Waldo |
| 7,202,086 B2 | 4/2007 | Delcourt et al. |
| 2003/0138843 A1* | 7/2003 | Waldo ............................. 435/7.1 |
| 2004/0048268 A1* | 3/2004 | Delcourt et al. .................. 435/6 |
| 2004/0078148 A1 | 4/2004 | Waldo |

FOREIGN PATENT DOCUMENTS

| | | | |
|---|---|---|---|
| EP | 1097990 | 5/2001 | |
| EP | 1097990 A2 * | 5/2001 | ............... C12N 9/12 |
| WO | WO 01/29225 | 4/2001 | |

OTHER PUBLICATIONS

Hillebrecht et al. (Directed evolution of bacteriorhodopsin for device applications, 2004, Methods in Enzymology, vol. 388, pp. 333-347).*
Sieber, Selection for soluble proteins via fusion with chloramphenicol acetyltransferase, in Methods in Molecular Biology, vol. 230, Methods of Enzymology, Eds. Arnold and Georgiou, 2003, Humana Press, pp. 45-46 and Title pages (4 total).*
Linden et al. (Single-step purification of a recombinant thermostable a-amylase after solubilization of the enzyme from insoluble aggregates, 2000, Journal of Chromatography B, vol. 737, pp. 253-259).*
Moreno et al. (Development of a gene expression vector for Thermus thermophilus based on the promoter of the respiratory nitrate reductase, 2003, Plasmid, vol. 49, pp. 2-8).*
Archaea, downloaded from The Earth Life Web at http://www.earthlife.net/prokaryotes/archaea.html , Jun. 21, 2017.*
French Biotech Companies Seminar, Osaka, Japan Mission, Oct. 20, 2003, pp. 1-5.
Liao, H., et al. "Isolation of a thermostable enzyme variant by cloning and selection in a thermophile" *Proc. Natl. Acad. Sci. USA*, Feb. 1986, pp. 576-580, vol. 83, XP-000971054.
Waldo, G. S. et al. "Rapid protein-folding assay using green fluorescent protein" *Nature Biotechnology*, Jul. 1999, pp. 691-695, vol. 17.
Omoya, K. et al. "Systematic optimization of active protein expression using GFP as a folding reporter" *Protein Expression and Purification*, Aug. 2004, pp. 327-332, vol. 36, No. 2.
Nakayama, M. et al. "A system using convertible vectors for screening soluble recombinant proteins produced in *Escherichia coli* from randomly fragmented cDNAs" *Biomedical and Biophysical Research Communications*, Dec. 19, 2003, pp. 825-830, vol. 312, No. 3.
Brouns, S. J. J. et al. "Engineering a selectable marker for hyperthermophiles" *Journal of Biological Chemistry*, Mar. 25, 2005, pp. 11422-11431, vol. 280, No. 12.
Linden, A. et al. "Single-step purification of a recombinant thermostable α-amylase after solubilization of the enzyme from insoluble aggregates" Journal of Chromatography B, 2000, pp. 253-259, vol. 737.
Pedelacq, J. et al. "Engineering soluble proteins for structural genomics" *Nature Biotechnology*, Sep. 2002, pp. 927-932, vol. 20.
Koschorreck, M. et al. "How to find soluble proteins: a comprehensive analysis of alpha/beta hydrolases for recombinant expression in *E. coli*" *BMC Genomics*, 2005, pp. 1-10, vol. 6, No. 49.
Roodveldt, C. et al. "Directed evolution of proteins for heterologous expression and stability" *Current Opinion in Structural Biology*, 2005, pp. 50-56, vol. 15.
Eijsink, V. G. H. et al. "Rational engineering of enzyme stability" *Journal of Biotechnology*, 2004, pp. 105-120, vol. 113.

(Continued)

*Primary Examiner* — Jennifer Pitrak McDonald
(74) *Attorney, Agent, or Firm* — Saliwanchik, Lloyd & Eisenschenk

(57) ABSTRACT

The invention relates to a method for selecting proteins stable in non-standard physicochemical conditions (temperature, pressure, pH, osmolarity, salinity, solvent, etc.) comprising the expression, in an extremophilic microorganism, of variants of the protein of interest in the form of a fusion protein with a reporter protein which is stable in extreme conditions and acts as a selection marker.

17 Claims, 14 Drawing Sheets

(56) References Cited

OTHER PUBLICATIONS

Figure 2:
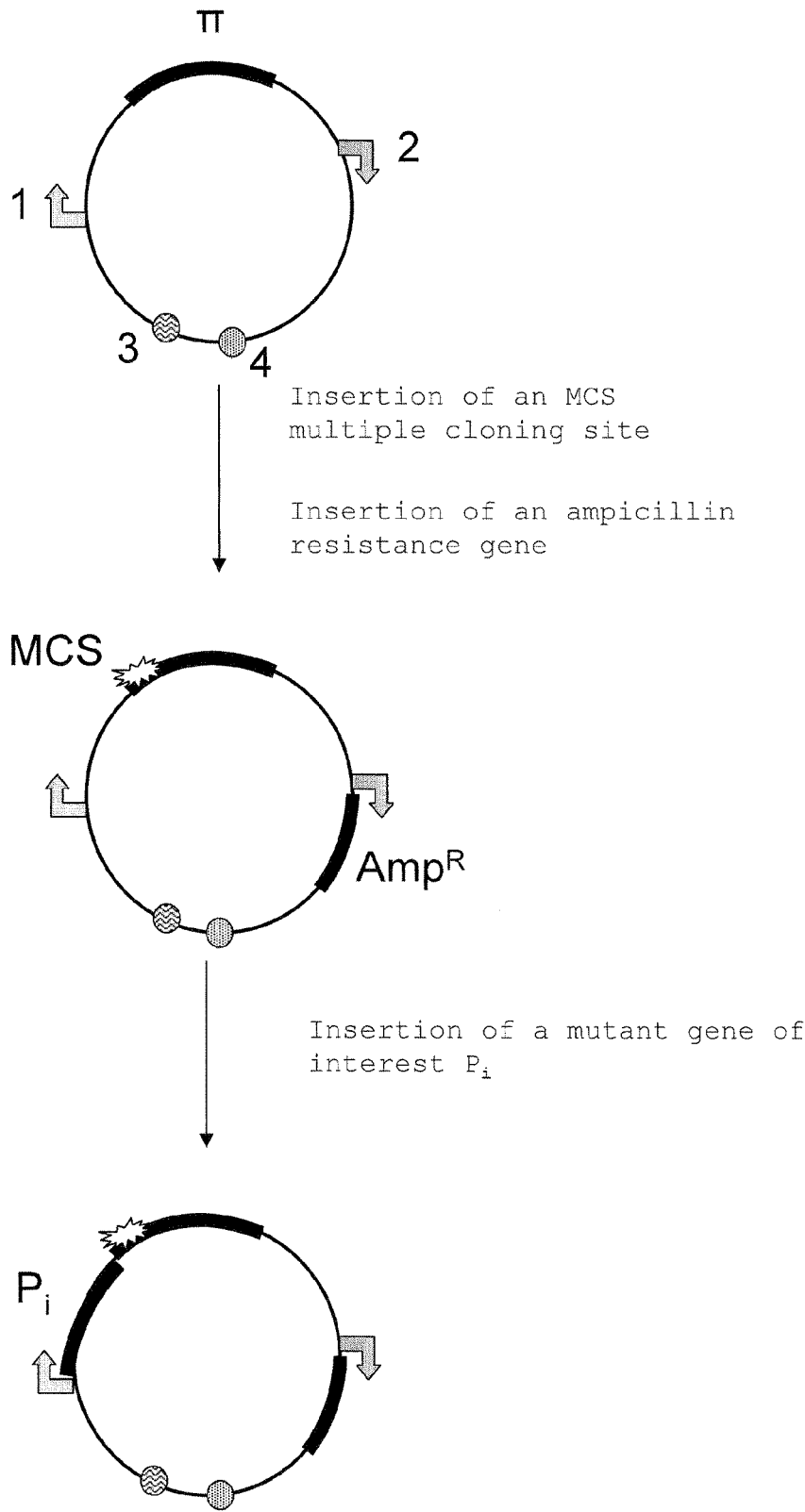

Sieber, V. et al. "Selecting proteins with improved stability by a phage-based method" *Nature Biotechnology*, Oct. 1998, pp. 955-960, vol. 16.
Gourevitch, A. et al. "Microbiological Studies With Kanamycin" *Annals of the New York Academy of Sciences*, Sep. 1958, pp. 31-41.

\* cited by examiner

Figure 1
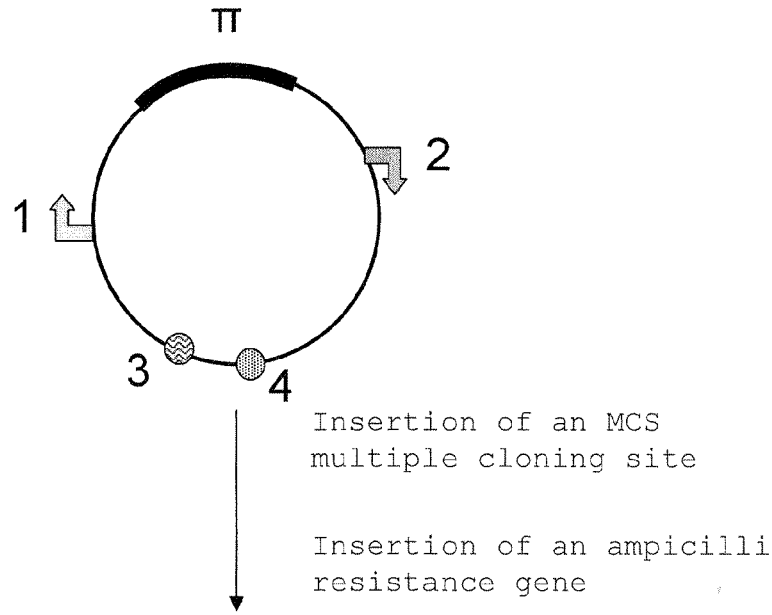
Insertion of an MCS multiple cloning site
Insertion of an ampicillin resistance gene
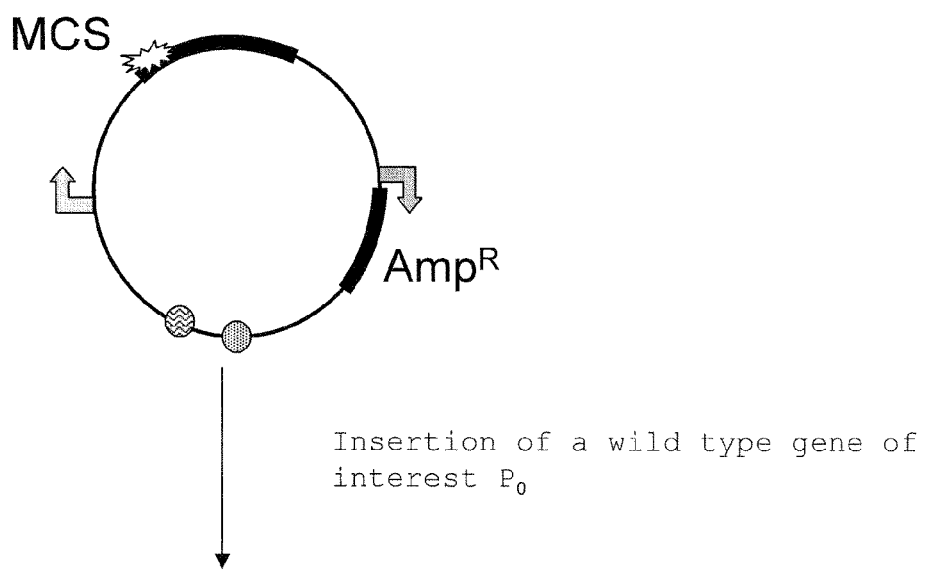
Insertion of a wild type gene of interest $P_0$
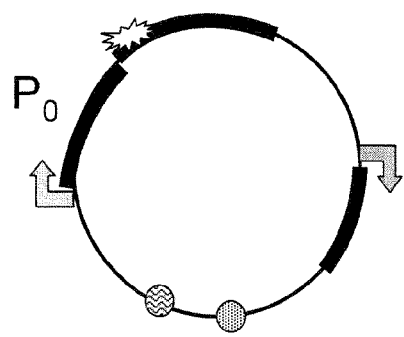

Figure 5
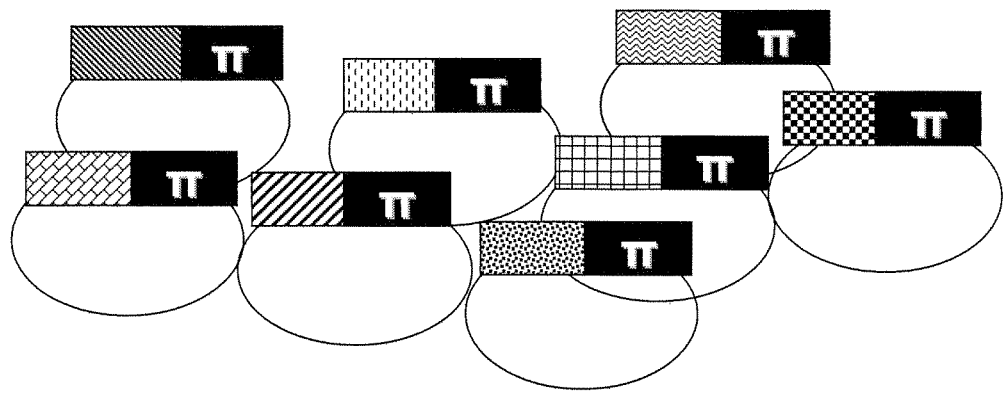
Transformation of competent bacteria (c)
Culture in selective medium (d)
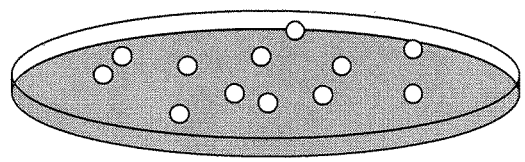

Figure 6
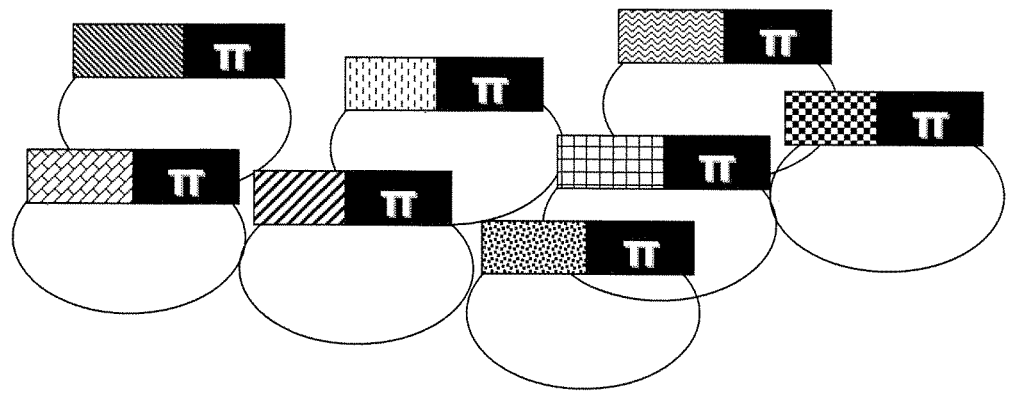
Transformation of competent bacteria (c)
Culture in selective medium (d)
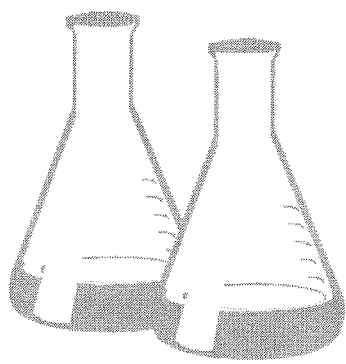

Figure 9
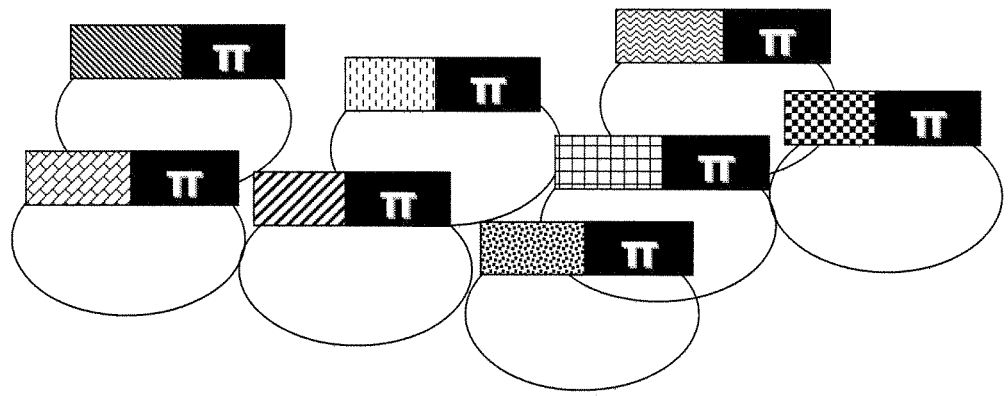
Transformation of competent bacteria (c)
Visualization of reporter protein (d)
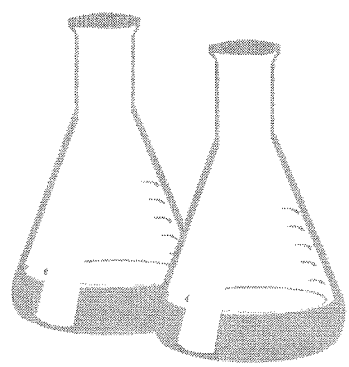

| Clone | Mutations | Low stringency: TF20 | High stringency: TF40 |
|---|---|---|---|
| pNCK-IFNγ | | 0,01 | <0,001 |
| pNCK-IFNΔ10 | Δ10 | 0,83 | 0,31 |
| pNCK-IFN::E30C/S92C | E30C, S92C | 0,65 | 0,29 |
| pNCK-IFNStop | M157Stop | <0,001 | <0,001 |
| | | | |
| L20_1 | D25V | 1,00 | 0,07 |
| L20_2 | V28C | 0,36 | 0,01 |
| L20_3 | W59F | 0,10 | <0,001 |
| L20_4 | S63D | 0,38 | 0,04 |
| L20_5 | E98K | 0,34 | 0,06 |
| L20_6 | S165V | 0,26 | <0,001 |
| L20_7 | Y22D, S122H | 0,55 | 0,50 |
| L20_8 | P26D, S122P | 0,03 | <0,001 |
| L20_9 | Y76D, K131I | 0,31 | 0,01 |
| L20_10 | R162Q, A164E | 0,85 | 0,08 |
| L20_11 | Y22S, L158W, R163G | 0,70 | <0,001 |
| L20_12 | T50Y, Y121T, M140P | 0,40 | 0,53 |
| L20_13 | Y22T, K109C, T119P, A147F, R163L | 0,10 | <0,001 |
| | | | |
| L40_1 | C21W | 0,55 | 0,63 |
| L40_2 | Q24A | 1,08 | 1,96 |
| L40_3 | R162E | 0,77 | 0,41 |
| L40_4 | R163T | 0,75 | 0,31 |
| L40_5 | C21G, F159C | 0,71 | 0,68 |
| L40_6 | M100N, T119Y | 0,98 | 0,98 |
| L40_7 | A147E, R162D | 0,09 | <0,001 |

Figure 12

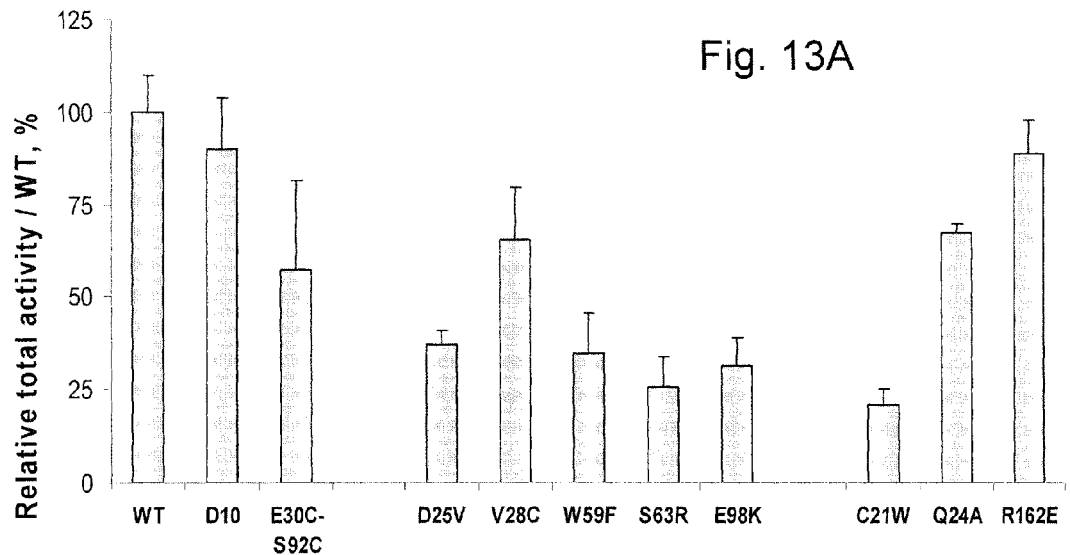
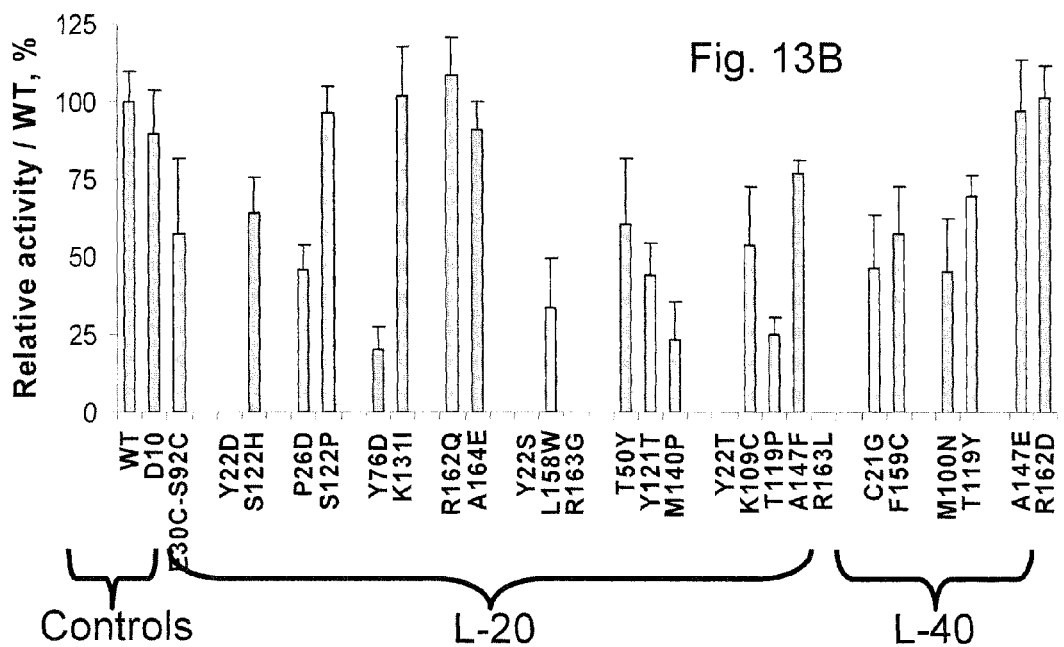

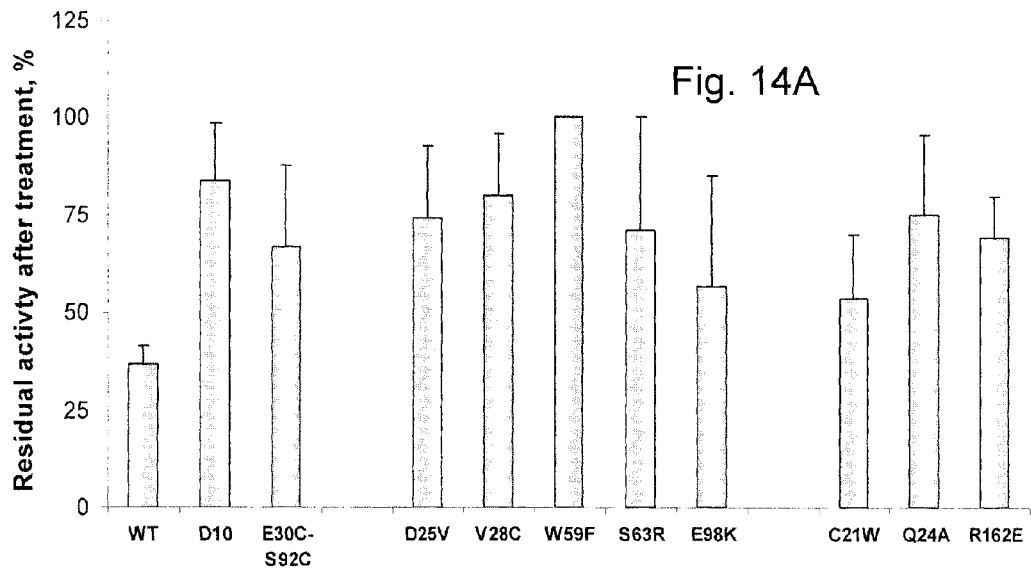
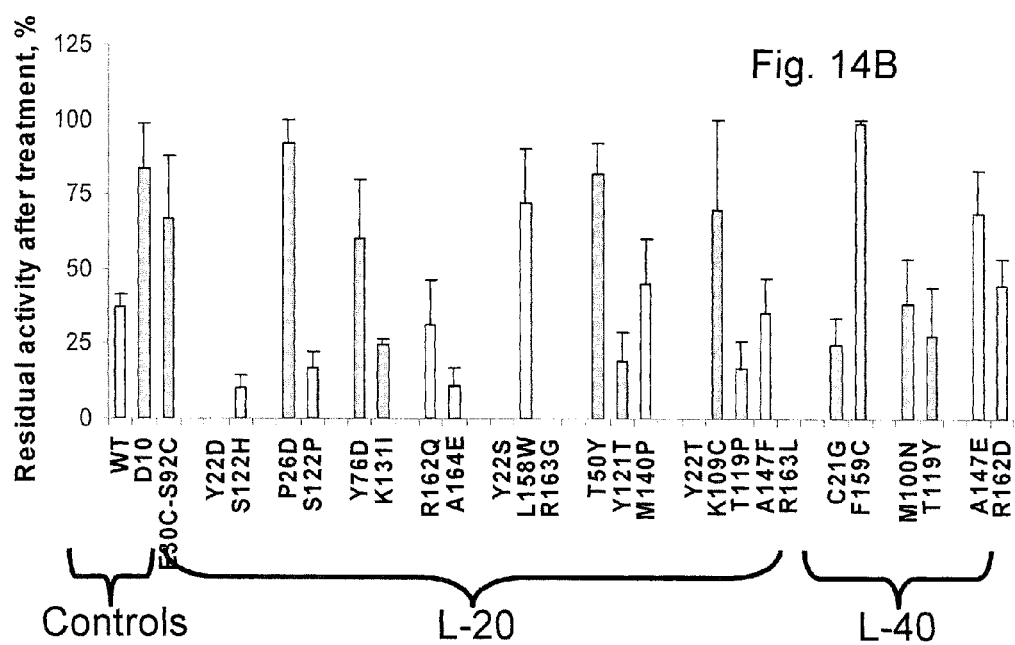
Figure 14

SEQUENCE LISTING

<160> NUMBER OF SEQ ID NOS: 8

<210> SEQ ID NO 1
<211> LENGTH: 744
<212> TYPE: DNA
<213> ORGANISM: artificial sequence
<220> FEATURE:
<223> OTHER INFORMATION: thermoresistant variant of kanamycin resistance
      gene
<220> FEATURE:
<221> NAME/KEY: CDS
<222> LOCATION: (1)..(744)
<223> OTHER INFORMATION:

<400> SEQUENCE: 1

```
atg act aga gaa gaa aga atg aag att gtt cat gaa att aag gaa cga      48
Met Thr Arg Glu Glu Arg Met Lys Ile Val His Glu Ile Lys Glu Arg
1               5                   10                  15 ata ttg gat aaa tat ggg gat gat gtt aag gct att ggt gtt tat ggc      96
Ile Leu Asp Lys Tyr Gly Asp Asp Val Lys Ala Ile Gly Val Tyr Gly
            20                  25                  30 tct ctt ggt cgt cag act gat ggg ccc tat tcg gat att gag atg atg    144
Ser Leu Gly Arg Gln Thr Asp Gly Pro Tyr Ser Asp Ile Glu Met Met
        35                  40                  45 tgt gtc atg tca aca gag gaa gca gag ttc agc cat gaa tgg aca acc    192
Cys Val Met Ser Thr Glu Glu Ala Glu Phe Ser His Glu Trp Thr Thr
    50                  55                  60 ggt gag tgg aag gtg gaa gtg aat ttt tat agc gaa gag att cta cta    240
Gly Glu Trp Lys Val Glu Val Asn Phe Tyr Ser Glu Glu Ile Leu Leu
65                  70                  75                  80 gat tat gca tct cag gtg gaa tca gat tgg ccg ctt aca cat ggt caa    288
Asp Tyr Ala Ser Gln Val Glu Ser Asp Trp Pro Leu Thr His Gly Gln
                85                  90                  95 ttt ttc tct att ttg ccg att tat gat tca ggt gga tac tta gag aaa    336
Phe Phe Ser Ile Leu Pro Ile Tyr Asp Ser Gly Gly Tyr Leu Glu Lys
            100                 105                 110 gtg tat caa act gct aaa tcg gta gaa gcc caa aag ttc cac gat gcg    384
Val Tyr Gln Thr Ala Lys Ser Val Glu Ala Gln Lys Phe His Asp Ala
        115                 120                 125 att tgt gcc ctt atc gta gaa gag ctg ttt gaa tat gca ggc aaa tgg    432
Ile Cys Ala Leu Ile Val Glu Glu Leu Phe Glu Tyr Ala Gly Lys Trp
    130                 135                 140 cgt aat att cgt gtg caa gga ccg aca aca ttt cta cca tcc ttg act    480
Arg Asn Ile Arg Val Gln Gly Pro Thr Thr Phe Leu Pro Ser Leu Thr
145                 150                 155                 160 gta cag gta gca atg gca ggt gcc atg ttg att ggt ctg cat cat cgc    528
Val Gln Val Ala Met Ala Gly Ala Met Leu Ile Gly Leu His His Arg
                165                 170                 175 atc tgt tat acg acg agc gct tcg ctc tta act gaa gca gtt aag caa    576
Ile Cys Tyr Thr Thr Ser Ala Ser Leu Leu Thr Glu Ala Val Lys Gln
            180                 185                 190 tca gat ctt cct tca ggt tat gac cat ctg tgc cag ttc gta atg tct    624
Ser Asp Leu Pro Ser Gly Tyr Asp His Leu Cys Gln Phe Val Met Ser
        195                 200                 205 ggt caa ctt tcc gac tct gag aaa ctt ctg gaa tcg cta gag aat ttc    672
Gly Gln Leu Ser Asp Ser Glu Lys Leu Leu Glu Ser Leu Glu Asn Phe
    210                 215                 220 tgg aat ggg att cag gag tgg aca gaa cga cac gga tat ata gtg gat    720
Trp Asn Gly Ile Gln Glu Trp Thr Glu Arg His Gly Tyr Ile Val Asp
225                 230                 235                 240 gtg tca aaa cgc ata cca ttt tga                                      744
Val Ser Lys Arg Ile Pro Phe
```

245

<210> SEQ ID NO 2
<211> LENGTH: 247
<212> TYPE: PRT
<213> ORGANISM: artificial sequence
<220> FEATURE:
<223> OTHER INFORMATION: thermoresistant variant of kanamycin resistance
      gene

<400> SEQUENCE: 2

Met Thr Arg Glu Glu Arg Met Lys Ile Val His Glu Ile Lys Glu Arg
1               5                   10                  15

Ile Leu Asp Lys Tyr Gly Asp Val Lys Ala Ile Gly Val Tyr Gly
            20                  25                  30

Ser Leu Gly Arg Gln Thr Asp Gly Pro Tyr Ser Asp Ile Glu Met Met
        35                  40                  45

Cys Val Met Ser Thr Glu Glu Ala Glu Phe Ser His Glu Trp Thr Thr
    50                  55                  60

Gly Glu Trp Lys Val Glu Val Asn Phe Tyr Ser Glu Glu Ile Leu Leu
65                  70                  75                  80

Asp Tyr Ala Ser Gln Val Glu Ser Asp Trp Pro Leu Thr His Gly Gln
                85                  90                  95

Phe Phe Ser Ile Leu Pro Ile Tyr Asp Ser Gly Gly Tyr Leu Glu Lys
            100                 105                 110

Val Tyr Gln Thr Ala Lys Ser Val Glu Ala Gln Lys Phe His Asp Ala
        115                 120                 125

Ile Cys Ala Leu Ile Val Glu Leu Phe Glu Tyr Ala Gly Lys Trp
    130                 135                 140

Arg Asn Ile Arg Val Gln Gly Pro Thr Thr Phe Leu Pro Ser Leu Thr
145                 150                 155                 160

Val Gln Val Ala Met Ala Gly Ala Met Leu Ile Gly Leu His Arg
                165                 170                 175

Ile Cys Tyr Thr Thr Ser Ala Ser Leu Leu Thr Glu Ala Val Lys Gln
            180                 185                 190

Ser Asp Leu Pro Ser Gly Tyr Asp His Leu Cys Gln Phe Val Met Ser
        195                 200                 205

Gly Gln Leu Ser Asp Ser Glu Lys Leu Leu Glu Ser Leu Glu Asn Phe
    210                 215                 220

Trp Asn Gly Ile Gln Glu Trp Thr Glu Arg His Gly Tyr Ile Val Asp
225                 230                 235                 240

Val Ser Lys Arg Ile Pro Phe
                245

<210> SEQ ID NO 3
<211> LENGTH: 375
<212> TYPE: DNA
<213> ORGANISM: artificial sequence
<220> FEATURE:
<223> OTHER INFORMATION: thermoresistant variant of bleomycin resistance
      gene
<220> FEATURE:
<221> NAME/KEY: CDS
<222> LOCATION: (1)..(375)
<223> OTHER INFORMATION:

<400> SEQUENCE: 3 atg gct aaa ctt act tct gct gtt cct gtt ctt aca gct aga gat gta    48
Met Ala Lys Leu Thr Ser Ala Val Pro Val Leu Thr Ala Arg Asp Val
1               5                   10                  15

```
gca gaa gct gtt gaa ttt tgg act gat aga ttg ggt ttt tct agg gtt        96
Ala Glu Ala Val Glu Phe Trp Thr Asp Arg Leu Gly Phe Ser Arg Val
         20                  25                  30 ttc gtg gaa gac gat ttt gca ggt gtt gtt aga gat gat gta aca ctt       144
Phe Val Glu Asp Asp Phe Ala Gly Val Val Arg Asp Asp Val Thr Leu
 35                  40                  45 ttt att tca gct gtg caa gat caa gtt gtt cca gat aat act caa gca       192
Phe Ile Ser Ala Val Gln Asp Gln Val Val Pro Asp Asn Thr Gln Ala
 50                  55                  60 tgg gta tgg gtt aga ggt ttg gat gag ctt tat gct gaa tgg tct gaa       240
Trp Val Trp Val Arg Gly Leu Asp Glu Leu Tyr Ala Glu Trp Ser Glu
65                  70                  75                  80 gtt gtg tct aca aat ttt agg gat gca agt ggt cct gct atg act gag       288
Val Val Ser Thr Asn Phe Arg Asp Ala Ser Gly Pro Ala Met Thr Glu
                 85                  90                  95 att gtt gaa caa cct tgg ggt aga gaa ttt gca ctt aga gat cct gct       336
Ile Val Glu Gln Pro Trp Gly Arg Glu Phe Ala Leu Arg Asp Pro Ala
                100                 105                 110 ggt aat tgt gtt cat ttt gtt gca gag gaa caa gat tga                   375
Gly Asn Cys Val His Phe Val Ala Glu Glu Gln Asp
            115                 120

<210> SEQ ID NO 4
<211> LENGTH: 124
<212> TYPE: PRT
<213> ORGANISM: artificial sequence
<220> FEATURE:
<223> OTHER INFORMATION: thermoresistant variant of bleomycin resistance
      gene

<400> SEQUENCE: 4

Met Ala Lys Leu Thr Ser Ala Val Pro Val Leu Thr Ala Arg Asp Val
1               5                   10                  15

Ala Glu Ala Val Glu Phe Trp Thr Asp Arg Leu Gly Phe Ser Arg Val
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Gln Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Val Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 5
<211> LENGTH: 441
<212> TYPE: DNA
<213> ORGANISM: Homo sapiens
<220> FEATURE:
<221> NAME/KEY: CDS
<222> LOCATION: (1)..(441)
<223> OTHER INFORMATION:

<400> SEQUENCE: 5 tgt tac tgc cag gac cca tat gta caa gaa gca gaa aac ctt aag aaa        48
Cys Tyr Cys Gln Asp Pro Tyr Val Gln Glu Ala Glu Asn Leu Lys Lys
1               5                   10                  15
```

```
tat ttt aat gca ggt cat tca gat gta gcg gat aat gga act ctt ttc      96
Tyr Phe Asn Ala Gly His Ser Asp Val Ala Asp Asn Gly Thr Leu Phe
             20                  25                  30 tta ggc att ttg aag aat tgg aaa gag gag agt gac aga aaa ata atg     144
Leu Gly Ile Leu Lys Asn Trp Lys Glu Glu Ser Asp Arg Lys Ile Met
         35                  40                  45 cag agc caa att gtc tcc ttt tac ttc aaa ctt ttt aaa aac ttt aaa     192
Gln Ser Gln Ile Val Ser Phe Tyr Phe Lys Leu Phe Lys Asn Phe Lys
     50                  55                  60 gat gac cag agc atc caa aag agt gtg gag acc atc aag gaa gac atg     240
Asp Asp Gln Ser Ile Gln Lys Ser Val Glu Thr Ile Lys Glu Asp Met
65                  70                  75                  80 aat gtc aag ttt ttc aat agc aac aaa aag aaa cga gat gac ttc gaa     288
Asn Val Lys Phe Phe Asn Ser Asn Lys Lys Lys Arg Asp Asp Phe Glu
                 85                  90                  95 aag ctg act aat tat tcg gta act gac ttg aat gtc caa cgc aaa gca     336
Lys Leu Thr Asn Tyr Ser Val Thr Asp Leu Asn Val Gln Arg Lys Ala
            100                 105                 110 ata cat gaa ctc atc caa gtg atg gct gaa ctg tcg cca gca gct aaa     384
Ile His Glu Leu Ile Gln Val Met Ala Glu Leu Ser Pro Ala Ala Lys
        115                 120                 125 aca ggg aag cga aaa agg agt cag atg ctg ttt cga ggt cga aga gca     432
Thr Gly Lys Arg Lys Arg Ser Gln Met Leu Phe Arg Gly Arg Arg Ala
    130                 135                 140 tcc cag taa                                                          441
Ser Gln
145

<210> SEQ ID NO 6
<211> LENGTH: 146
<212> TYPE: PRT
<213> ORGANISM: Homo sapiens

<400> SEQUENCE: 6

Cys Tyr Cys Gln Asp Pro Tyr Val Gln Glu Ala Glu Asn Leu Lys Lys
1               5                   10                  15

Tyr Phe Asn Ala Gly His Ser Asp Val Ala Asp Asn Gly Thr Leu Phe
             20                  25                  30

Leu Gly Ile Leu Lys Asn Trp Lys Glu Glu Ser Asp Arg Lys Ile Met
         35                  40                  45

Gln Ser Gln Ile Val Ser Phe Tyr Phe Lys Leu Phe Lys Asn Phe Lys
     50                  55                  60

Asp Asp Gln Ser Ile Gln Lys Ser Val Glu Thr Ile Lys Glu Asp Met
65                  70                  75                  80

Asn Val Lys Phe Phe Asn Ser Asn Lys Lys Lys Arg Asp Asp Phe Glu
                 85                  90                  95

Lys Leu Thr Asn Tyr Ser Val Thr Asp Leu Asn Val Gln Arg Lys Ala
            100                 105                 110

Ile His Glu Leu Ile Gln Val Met Ala Glu Leu Ser Pro Ala Ala Lys
        115                 120                 125

Thr Gly Lys Arg Lys Arg Ser Gln Met Leu Phe Arg Gly Arg Arg Ala
    130                 135                 140

Ser Gln
145

<210> SEQ ID NO 7
<211> LENGTH: 27
<212> TYPE: DNA
```

```
<213> ORGANISM: artificial sequence
<220> FEATURE:
<223> OTHER INFORMATION: linker
<220> FEATURE:
<221> NAME/KEY: CDS
<222> LOCATION: (1)..(27)
<223> OTHER INFORMATION:

<400> SEQUENCE: 7 gcg gcc gca gga agc tct ggt tcc atc                                27
Ala Ala Ala Gly Ser Ser Gly Ser Ile
1               5

<210> SEQ ID NO 8
<211> LENGTH: 9
<212> TYPE: PRT
<213> ORGANISM: artificial sequence
<220> FEATURE:
<223> OTHER INFORMATION: linker

<400> SEQUENCE: 8

Ala Ala Ala Gly Ser Ser Gly Ser Ile
1               5
```

METHOD FOR SELECTING STABLE PROTEINS IN NON-STANDARD PHYSICOCHEMICAL CONDITIONS

CROSS-REFERENCE TO RELATED APPLICATION

This application is the U.S. national stage application of International Patent Application No. PCT/FR2006/000735, filed Apr. 4, 2006, the disclosure of which is hereby incorporated by reference in its entirety, including all figures, tables and amino acid or nucleic acid sequences.

INTRODUCTION

The invention relates to the field of molecular biology and more particularly to the directed evolution of proteins.

The annual market for industrial and specialty enzymes is estimated at several billion euros. Fewer than 30 enzymes account for more than 90% of industrial enzymes in use. However the great majority of these enzymes are labile and have low resistance when employed in industrial conditions, hence the search for more robust enzymes (temperature, pH, pressure) to serve as substitutes. Enzymes are used to supplement or replace heavier, classical chemical methods and by doing so they increase the accuracy and lower the costs of these processes and minimize the negative environmental impact. Many of these processes do not take place at neutral pH, room temperature or atmospheric pressure. The method according to the invention tailors enzymes to be compatible with a use in processes involving high temperature (50° C. to 110° C.) or low temperature (−5° C. to 15° C.) and/or increases the stability of enzymes at extreme pH or at high pressure or in the presence of a high NaCl or KCl concentration, or else in various solvents.

In another field, therapeutic proteins and antibodies represent a large and growing share of the pharmaceuticals market. A key challenge to improving hormones, enzymes, antibodies and other therapeutic proteins is to increase the in vivo stability thereof. This is because, if a therapeutic protein is rapidly degraded in the body, it is more difficult to regulate the active concentration at a given time and it becomes necessary to increase the dosing frequency, which is costly and diminishes patient comfort. The method according to the invention, by allowing the selection of proteins which are stable in non-standard physicochemical conditions, can indirectly enhance the in vivo stability of therapeutic proteins.

High temperatures and thermostable proteins are an important example of non-standard physicochemical conditions. Naturally occurring thermostable peptides and proteins are found in microorganisms which grow at extreme temperatures. Thermophilic microorganisms comprise in particular: *Bacillus stearothermophilus* (which lives at a temperature of up to Tmax~60° C.), *Thermus aquaticus* (Tmax~70° C.) and *Thermus thermophilus* (Tmax~80° C.), and hyper-thermophilic microorganisms such as *Thermotoga maritime* (Tmax~90° C.) and *Aquifex pyrophilus* (Tmax~95° C.). The ability of these microorganisms to grow at high temperatures implies that their enzymes and proteins are stable and active at such temperatures (Moreno R et al. Applied and Environmental Microbiology. 2004; 71:591-93). Said microorganisms are potential sources of various enzymes of industrial interest (Vieille C et al. Microbiol. Mol. Biol. Rev. 2001; 65:1-43; Sterner R et al Crit. Rev. Biochem. Mol. Biol. 2001; 36:39-106; Pantazaki A A et al. Appl. Microbiol. Biotechnol. 2002; 58:1-12; Niehaus F. et al. Appl. Microbiol. Biotechnol. 1999; 51:711-29).

The most well-known example of the use of proteins from extremophilic microorganisms is the case of the thermostable DNA polymerase enzymes in molecular biology. Thanks to the thermostable polymerase of *Thermus aquaticus* (Taq polymerase), the polymerase chain reaction (PCR)—which has revolutionized molecular biology—could be invented. Thermostable polymerases from other thermophilic microorganisms, including Pfu polymerase and Vent polymerase, have since been produced and commercialized. By recombining in vitro the sequences of different thermostable polymerases and using a selection method specific for said polymerases, one group has generated novel thermostable polymerases, with high thermostability, lower sensitivity to common inhibitors or else capable of incorporating non-standard nucleotides (Ghadessy F J et al. Proc. Natl. Acad. Sci. USA 2001; 98:4552-7; Ghadessy F J et al. Nat. Biotechnol. 2004; 22:755-9).

Another example of the use of an important enzyme originating from an extremophile is the case of cellulases derived from alkalophilic microorganisms, which are used as cellulose degradation agents in detergents (for example, cellulase 103, marketed by Genencor since 1997).

More generally, and without the following list of "extremozymes" being exhaustive, extremophilic microorganisms have been the source of many novel enzymes in recent years (Schiraldi C et al. Trends Biotechnol. 2002; 20:515-20; Van den Burg, B. Curr. Op. Microbiol. 2003; 6:213-18). For instance, thermophiles are the source of amylases and glycosidases, used in the treatment of starch and different oses, for the synthesis of oligosaccharides, of lipases used in waste water treatment or in some detergents, of xylanases used in the paper industry, of proteases used in the food processing industry for the production of amino acids and in some detergents. Moreover, the ability to carry out industrial processes at high temperature has the added advantage of less risk of microbial contamination, lower viscosity, higher transfer rates and increased substrate solubility. Psychrophilic microorganisms are the source of amylases, proteases and lipases used in detergents, of dehydrogenases used as biosensors. Alkalophiles are the source of cellulases and proteases used as polymer degradation agents in detergent formulations; of amylases and lipases used as food additives. Acidophiles are the source of amylases used in starch treatment and of oxidases used for carbon desulfurization. Halophiles are the source of proteases used in peptide synthesis, and of dehydrogenases used for biocatalysis in organic media (Marhuenda-Egea F C et al. Curr. Op. Biotech. 2002; 13:385-89). The ability to select enzymes which are active in the presence of high salt concentrations is important in the case of industrial processes where the enzymes are employed in the presence of high concentrations of substrates present in ionic form in the reaction medium.

The direct use of extremophilic bacteria or archaebacteria in order to isolate stable and/or active proteins in non-standard physicochemical conditions can therefore be efficient. Yet such an approach is rarely possible in the case of enzymes originating from eukaryotes, fungi, yeasts, plants or mammals: few extremophilic eukaryotes have been identified (but see http://www.nhm.ac.uk/zoology/extreme.html). In such cases one must start with a standard enzyme and then improve it, through directed evolution, to make it stable and/or active in non-standard physicochemical conditions. Said directed evolution approach for proteins stable in non-standard physicochemical conditions is not restricted to proteins from eukaryotes, which are generally mesophilic, but is also of interest for any proteins originating from common prokaryotes, which are also mesophilic. Despite all the advances in modern biology, it still remains difficult to elucidate the relationships between protein structure and function. In particular, it is not easy in practice to predict precisely which mutations will make a protein stable in non-standard physicochemical conditions. The best approach, in this context where a rational design is ineffective, is directed molecular evolution. Inspired by natural Darwinian evolution, directed evolution reproduces the principal steps thereof in the laboratory: generating genetic diversity, expressing the corresponding proteins, then sorting the products adapted to the defined conditions. Thus, directed evolution commences by creating genetic diversity, then expressing said genes and sorting the genes encoding proteins which are improved for a parameter of interest. Several types of generic methods are available to create diversity by modifying the sequence of an initial gene: random mutagenesis (Leung D W et al. Technique. 1989; 1:11-15; Cadwell R C et al. PCR Methods Appl. 1992; 2:28-33), site directed mutagenesis (Kunkel T A et al. J. Methods Enzymol. 1991; 204:125-39; Lacks et al. Methods Enzymol. 1980; 65:138; US2004253729), Massive Mutagenesis (WO0216606), elongation mutagenesis (Matsuura T et al. Nat. Biotechnol. 1999; 17:58-61). Other methods generate diversity by mixing up the sequences of several genes: in vitro recombination by DNA shuffling (Stemmer W P C. Proc. Natl. Acad. Sci. USA 1993; 91:10747-51; Stemmer W P C. Nature. 1994; 370:389-91; U.S. Pat. No. 5,605,793; U.S. Pat. No. 5,830,721; U.S. Pat. No. 6,506,603), StEP (U.S. Pat. No. 6,153,410; U.S. Pat. No. 6,177,263; Zhao et al. Nat. Biotechnol. 1998; 16:258-61; Aguinaldo A M et al. Methods Mol. Biol. 2003; 231:105-10), in vitro circular recombination (patent application FR 0503364 filed by Biomethodes). A third type of technique gives direct access to natural diversity without cultivating the corresponding microorganisms: metagenomics (Streitt W R et al. Curr. Opin. Biotechnol. 2004; 15:285-90; Daniel R et al. Curr. Opin. Biotechnol. 2004; 15:199-204). All of these methods for obtaining diversity are useful in the scope of generating, by the method of the invention, proteins that are stable in non-standard physicochemical conditions according to the invention. It will be noted that, in some cases, empirical data and results from existing limited models on protein sequence-structure-stability relationships can be incorporated into a mutagenesis strategy. For example, the comparison of sequences and structures of proteins with those of their thermostable counterparts often reveals differences in surface loops, the frequency of hydrophobic residues with branched side chains, the frequency of charged amino acids or the frequency of disulfide bridges and it is possible to incorporate this type of data when choosing the mutagenesis targets and the type of substitution to create.

Once diversity has been created in the coding polynucleotides, the second step of directed evolution, sorting, takes place at the protein level and can be carried out in two ways: screening, particularly high-throughput screening, and selection. Screening consists in sorting proteins and the corresponding genes one by one on the basis of a test typically performed in 96-, 384- or 1536-well microplates. Depending on the degree of automation, approximately $10^3$ to $10^5$ variants per day can be sorted in this manner. The so-called selection methods more closely resemble natural selection, in that they sort "in bulk", at the same time, all variants meeting a given criterion, and isolate them from the majority of variants, which are unimproved. In this manner it is possible to sort about $10^6$ and up to $10^{13}$ variants simultaneously. It is easy to see that selection methods, when available, make it far easier to sort a much larger diversity than screening methods. Selection methods like phage display or ribosome display are available when the parameter of interest is the affinity of the protein for a given ligand, and said methods have been used with success in the antibody field. Said methods have been adapted to the case of selecting for enzymatic activity or stability in standard conditions (Amstutz P et al J. Am. Chem. Soc. 2002; 124:9396-9403; Jung S et al. J. Mol. Biol. 1999; 294:163-180.5). However, with respect to stability and activity in non-standard physicochemical conditions, individual screening methods predominate and there is no universal selection method, independent of the function of the protein of interest. As noted earlier, said screening methods are intensive, require a fair amount of equipment and are costly, and the libraries they generate are small. Having a universal selection method for proteins stable in non-standard physicochemical conditions would thus represent a qualitative leap in the field of directed protein evolution, and in particular of industrial enzymes, therapeutic proteins, biosensors and diagnostics. The use of such a method, together with existing methods for creating genetic diversity, would provide a large number of highly diverse novel proteins of major therapeutic or industrial interest by directed evolution. Such is precisely the object of the method according to the invention.

SUMMARY OF THE INVENTION

The method according to the invention is a method for selecting stable proteins, in particular in non-standard physicochemical conditions (temperature, pressure, pH, osmolarity, salinity, solvent, etc.), characterized by the expression, in an extremophilic microorganism, of variants of the protein of interest in the form of a fusion protein with a reporter protein Π which is stable in non-standard conditions acting as selection marker.

Thus, the invention relates to a method for selecting stable proteins, in particular in non-standard physicochemical conditions, characterized in that a library of variants of a protein of interest is expressed in an extremophilic microorganism as a fusion protein with a reporter protein which is stable in non-standard physicochemical conditions, and in that, one or several stable variants of the protein of interest are selected from the microorganisms in which the reporter protein is active.

Preferably, the extremophilic microorganisms has one or more of the following characteristics: thermophilic, hyperthermophilic, osmophilic, halophilic, psychrophilic, alkalophilic, piezophilic, radiophilic, and metallophilic. The extremophilic microorganism can be a bacteria, an archaebacteria, or an extremophilic eukaryote. In a preferred embodiment, the microorganism is a thermophilic or hyperthermophilic microorganism. In particular, the thermophilic or hyper-thermophilic microorganism can be selected in the group consisting of the following thermophilic or hyper-thermophilic microorganisms: *Thermus aquaticus, Thermus thermophilus, Thermotoga maritime* or *Aquifex pyrophilus*.

Preferably, the stable reporter protein is a protein whose correct expression allows the survival of the microorganism and the selection of the stable variant of the protein of interest is performed by the survival of the microorganism. In a preferred embodiment, the reporter protein is a protein conferring resistance to an antibiotic. For example, the reporter protein can be a thermostable version of a protein conferring resistance to an antibiotic. Preferably, the reporter protein is a thermostable version of a kanamycin or bleomycin resistance protein. In a more preferred embodiment, the reporter protein is a thermostable kanamycin nucleotidyltransferase. In an alternative embodiment, the reporter protein is an auxotrophy marker.

In another embodiment, the reporter protein is a protein whose correct expression directly or indirectly leads to the transformation of a substrate into a product, said product and substrate having different colors, and the selection of the stable variant of the protein of interest is performed by the color of the microorganisms. For example, the reporter protein can be a version of beta-galactosidase which is stable in non-standard physicochemical conditions.

In a further embodiment, the reporter protein is fluorescent or luminescent and the selection of the stable variant of the protein of interest is performed by detecting fluorescence or luminescence. The reporter protein can be non-fluorescent or non-luminescent in non-standard physicochemical conditions where it is produced but become fluorescent when it is placed in standard physicochemical conditions. Preferably, the reporter protein is GFP (green fluorescent protein) or a variant of GFP. In a preferred embodiment, the selection is performed by using FACS or by simple visual selection of bacterial colonies.

In a preferred embodiment, the protein of interest can be located at the N-terminal of the reporter protein in the fusion protein. In an alternative embodiment, the protein of interest is located at the C-terminal of the reporter protein in the fusion protein. Optionally, the fusion protein comprises a peptide linker.

The library of variants of the protein of interest can be generated by a mutagenesis technique known to those skilled in the art, preferably selected from the following: Massive Mutagenesis®, random mutagenesis, site directed mutagenesis, saturation mutagenesis, elongation mutagenesis, and in vivo mutagenesis, an in vivo or in vitro genetic recombination method, or a combination thereof. In a preferred embodiment, it is generated by Massive Mutagenesis® technology. In an alternative preferred embodiment, it is generated by in vitro circular recombination of several natural or synthetic genes encoding the protein of interest.

The library of variants of the protein of interest can also be created by direct cloning of nucleic acids from an environmental source using metagenomics technologies.

In a preferred embodiment, the microorganism is thermophilic or hyper-thermophilic, the reporter protein is a thermostable protein conferring resistance to an antibiotic, the protein of interest is located at the N-terminal of the reporter protein in the fusion protein, and the library of variants of the protein of interest is created by Massive Mutagenesis®. Preferably, the microorganism is *T. thermophilus*, the reporter protein is a thermostable kanamycin nucleotidyltransferase, and the fusion protein comprises a peptide linker.

The invention relates to proteins having increased stability in non-standard physicochemical conditions selected according to the method of the invention. Encompassed in particular, are the enzymes, antibodies, hormones, cytokines or other therapeutic proteins selected according to the inventive method and which have improved stability in vivo.

The invention also relates to a fusion protein such as described in the invention. In particular, the invention relates to a fusion protein comprising a protein of interest or a variant thereof and a thermostable version of a protein conferring resistance to an antibiotic. Preferably, the protein conferring resistance to an antibiotic is kanamycin nucleotidyltransferase or the bleomycin resistance protein. The invention also relates to a nucleic acid or expression vector encoding a fusion protein according to the invention. Preferably, the vector comprises the elements necessary for replication in an extremophilic microorganism. Optionally, the vector can also comprise an origin of replication for another microorganism commonly used in the laboratory, for example *E. coli*, and/or another antibiotic resistance gene, for example an ampicillin resistance gene.

DETAILED DESCRIPTION OF THE INVENTION

The method according to the invention allows the selection, within a group of variants of a protein of interest, of variants displaying increased stability in non-standard physicochemical conditions. Said non-standard or "extreme" physicochemical conditions are defined herein by: a high temperature (50° C. to 110° C.), a low temperature (−5° C. to 15° C.), an acidic medium (pH 0-5) or an alkaline medium (pH 9-14), a pressure several tenfold greater than atmospheric pressure, a high salt medium ([NaCl]>1M; [KCl]>1M, etc.), an aqueous organic or non-aqueous solvent, or any other conditions which are not usually encountered when cultivating classical microorganisms in the laboratory. For example, *Escherichia coli* does not grow in such non-standard conditions.

Said stability in more or less extreme media can be interesting and desirable in and of itself. In many cases, the selection for increased stability in non-standard physicochemical conditions may also indirectly lead to an improvement of the characteristics of the protein in other non-standard conditions, or in standard conditions. For instance, it has been shown that a variant which has acquired thermostability can also have acquired resistance to solvents (Liu et al, 2006; Hao et al, 2004), to detergents (Liao, 1993), to proteolysis (Mukherjee et al, 2005; Amin et al, 2004). Thermostability is also associated with a longer half-life in low stringency conditions (Hao et al, 2004; Wintrode et al, 2001). The method according to the invention therefore allows to improve protein stability, in the broad sense.

More specifically, starting from a gene $G_0$ encoding the protein of interest $P_0$ which one would like to improve, the inventive method comprises the following three steps:

a) starting from the gene of interest $G_0$, preparation of a library of variants $G_i$ encoding protein variants $P_i$ (where i=1, 2, . . . N with N comprised between 2 or 10 and $10^{10}$, and preferably comprised between $10^3$ and $10^8$) in a vector in such a way that the proteins $P_i$ are expressed with a reporter protein Π in the form of fusion proteins $P_i$-Π.

b) transformation of the vector library obtained in step a) into an extremophilic microorganism and expression of fusion proteins $P_i$-Π in defined non-standard physicochemical conditions, which are compatible with the conditions of life of the extremophilic microorganism.

c) selection, based on the activity of Π, of clones correctly expressing the fusion protein $P_i$-Π.

In a first embodiment, the preparation of the library of variants in step a) comprises the following steps: preparation of a construct or vector comprising the gene $G_0$ encoding the protein of interest $P_0$ and the sequence coding for a reporter protein Π in the form of a fusion protein $P_0$-Π, followed by the generation of a library of variants $G_i$ (where i=1, 2, . . . N with N comprised between 2 or 10 and $10^{10}$, and preferably comprised between $10^3$ and $10^8$) from said construct or said vector.

In an alternative embodiment, the preparation of the library of variants in step a) comprises the following steps: construction of a library of variants $G_i$ (where i=, 2, ... N with N comprised between 2 or 10 and $10^{10}$, and preferably comprised between $10^3$ and $10^8$), followed by cloning of the genes $G_i$ encoding the protein variants $P_i$ (1-1, 2, ... N) into a vector in such a way that the proteins $P_i$ are expressed with a reporter protein Π, stable in non-standard physicochemical conditions, as fusion proteins $P_i$-Π.

In a particular embodiment, the target parameter for improvement is thermostability, the extremophile is a thermophile and, starting from gene $G_0$ encoding protein $P_0$ which one would like to improve, the method according to the invention is characterized by the following three steps:
a) starting from the gene of interest $G_0$, preparation of a library of variants $G_i$ encoding protein variants $P_i$ (where i=1, 2, ... N with N comprised between 2 or 10 and $10^{10}$, and preferably comprised between $10^3$ and $10^8$) in a vector in such a way that the proteins $P_i$ are expressed with a reporter protein Π in the form of fusion proteins $P_i$-Π.
b) transformation of the vector library obtained in step a) into a thermophilic microorganism and expression of fusion proteins $P_i$-Π at high temperature.
c) selection, based on the activity of protein Π at high temperature, of clones correctly expressing the fusion protein $P_i$-Π.

A fairly similar approach is described in the literature in the case of improving the solubility of insoluble proteins: in these examples, the mutant libraries are fused in frame with GFP, and the mutants having acquired some solubility are selected by their higher fluorescence (U.S. Pat. Nos. 6,867,042 and 6,448,087; US patent applications 20030138843 and 20040078148).

The present invention differs in an important respect in that herein it is not improved protein solubility which is the target parameter, but rather improved stability in extreme conditions. In this respect, the selection hosts used are extremophilic microorganisms which are not mentioned in the aforecited documents. Furthermore, the method requires the design of shuttle vectors adapted to extremophilic microorganisms, but preferably also adapted to a standard microorganism like *E. Coli*. The fusion gene must correspond to the chosen non-standard conditions. Thus, the reporter gene Π must be stable in the non-standard physicochemical conditions used. In fact, the method according to the invention can be used to improve different parameters, such as thermostability, stability at low temperature, stability at extreme pH or else stability in the presence of high salt concentrations. While optimizing a protein so that it is stable and/or active in one of said conditions can lead to improved solubility, the reverse is generally not true. For instance, many proteins are very easily expressed in a heterologous manner in *E. coli* and are therefore very soluble without necessarily being stable in non-standard physicochemical conditions, in particular without being thermostable. Moreover, the sequence effects of improving activity at low temperature and at high temperature are obviously different. This difference can be further illustrated by considering the case of proteins which are highly thermostable but not very soluble (see for example: Linden A. et al. J. Chromatogr. B Biomed. Sci. Appl. 2000; January 14; 737(1-2):253-9). An analysis of the structural determinants of thermostability shows in fact that this parameter is related to greater solubility but also to a more compact conformation (Gromiha M M et al. Biophys. Chem. 1999; 82:51-67).

The detailed mechanisms ensuring the coupling between the stability of the two partners of a fusion protein remain obscure. Nevertheless, it has been observed that when a protein of interest is fused to a reporter protein, the conformation of one and the other are linked, generally in an order: a correct conformation of the protein located at the COOH end is dependent on the also correct conformation of the protein located at the $NH_2$ extremity. These conformational effects during synthesis have sometimes been described using the term "nucleation". In less frequent cases, however, the opposite is observed, so that an empirical approach consisting in testing both orientations is necessary to determine the direction of causality.

The proteins $P_i$ stable in the chosen non-standard physicochemical conditions may, concomitant to their increased stability, have decreased activity (that is to say, enzymatic activity, or affinity, in the case of antibodies, for example). It is sometimes desirable to obtain proteins which are not only stable but also active in non-standard physicochemical conditions. In this case, the generic method for selecting for stability provided by the inventive method must be followed by a second screening (or selection) of clones improved for the activity parameter. Said second screening can be performed directly on the $P_i$ protein fused with the reporter gene. Alternatively, it may be necessary at this stage to transpose the mutations identified in the stable $P_i$ proteins into another vector, optionally adapted to expression in another host (mammalian cells, yeasts, or other bacteria for example), by subcloning or by site directed mutagenesis. In particular, said transposition is desirable when the fusion with a reporter gene affects the activity of the protein of interest.

When a protein $P_i$ is not stable in a given set of non-standard physicochemical conditions, the fusion protein $P_i$-Π will not be stable. By selecting in the library those fusion proteins $P_i$-Π which correspond to a stable (or, as the case may be, active) protein Π, the method according to the invention allows the selection of $P_i$ proteins which are stable in said defined non-standard physicochemical conditions.

The first obvious constraint for the protein Π is that it must be stable in the conditions of selection. For example, if one wants to select a protein $P_i$ stable at 80° C., then the protein Π must itself be stable at a temperature of 80° C. or higher. In order for the thermostable protein Π to act as selection marker, it is also necessary to be able to easily isolate clones correctly expressing said protein from among clones which do not express it.

The simplest solution is selection by survival: when the protein Π is active, the extremophilic microorganism in which selection takes place survives, otherwise it dies. If the protein $P_i$ is stable in the chosen non-standard physicochemical conditions, then the fusion protein $P_i$-Π is expressed correctly at step b), which allows the protein Π to be active and the cells to survive. Such that in step c), the selection consists simply in recovering the cells which grew.

In this context a simple method is to use an antibiotic resistance protein. In step c), the selection is performed by cultivating the cells of the extremophilic microorganism used in liquid medium or solid medium, in the presence of the corresponding antibiotic. Only those cells which correctly express the resistance gene to this antibiotic in the chosen non-standard physicochemical conditions will grow.

For example, if the desired property is thermostability, one antibiotic for which thermostable variants of the resistance enzyme are known to exist is kanamycin. Kanamycin is an inexpensive antibiotic commonly used in research laboratories. It is a potent bactericidal agent acting independently of bacterial density, and having both a very potent and very rapid effect in vitro. Kanamycin nucleotidyltransferase (KNTase) is an enzyme which allows bacteria to resist the antibiotic. Said enzyme has been isolated from *Staphylococcus aureus*. It catalyses the transfer of a nucleoside monophosphate of a nucleotide to the 4' hydroxyl group of kanamycin. This neutralizes the effect of the antibiotic. Different mutants of the resistance enzyme exist which are stable and active at temperatures of up to more than 70° C. (Liao H H Enzyme Microb. Technol. 1993; 15:286-92; Sakon J et al. Biochemistry. 1993; 32; 11977-84; Liao H H et al. Proc. Natl. Acad. Sci. USA 1986; 83:576-580). The nucleotide and amino acid sequences of a thermostable kanamycin nucleotidyltransferase are exemplified by the sequences described in SEQ ID No. 1 and 2. Other thermostable kanamycin resistance genes have also been described (Hoseki J et al. J. Biochem. 1999; 126:951-6). It should be noted that kanamycin itself is stable at these high temperatures. The variants of a protein of interest which are thermostable and fused with thermostable KNTase allow the thermophilic microorganism to survive at high temperature in the presence of kanamycin. Conversely, non-thermostable variants of the protein of interest prevent the thermostable KNTase from being correctly expressed and the thermophilic microorganism dies. This direct selection by survival is remarkable in that it provides a very clearcut discrimination between the different variants of the protein, which allows the direct selection of clones expressing thermostable variants of the protein of interest.

Today it is possible to produce other proteins conferring antibiotic resistance to extremophilic microorganisms (bacteria or archaebacteria), and in particular thermophiles. For example, evolution of the equivalent protein from the mesophilic bacteria *Streptoalloteichus hindustamus* led to a protein conferring bleomycin resistance to the thermophilic bacteria *Thermus thermophilus* HB27 (Brouns et al. J. Biol. Chem. 2005; 280:11422-31). The nucleotide and amino acid sequences conferring thermostable bleomycin resistance are for example the sequences described in SEQ ID No. 3 and 4.

Through the use of selection methods well known to those skilled in the art, it is more generally possible to produce proteins conferring antibiotic resistance to various extremophilic microorganisms. For example, a library of mutants of the resistance gene which one would like to adapt to the extreme conditions of the microorganism of interest is cloned, the extremophilic microorganism is transformed with said library and the cells of said microorganism which grow in the presence of the antibiotic will harbor variants which are stable and active in the conditions of life of said microorganism. For example, Brouns et al. (Brouns et al., supra) describe a simple method for obtaining, by directed evolution, a gene conferring antibiotic resistance at high temperature. This provides a simple way to generate a range of proteins Π with the aid of which the inventive method will allow the selection of proteins stable in different non-standard physicochemical conditions.

In a particular embodiment, as an alternative to the use of antibiotics, the selection by survival is performed using auxotrophic strains. Said strains have been modified by deletion of a gene, the deletion being lethal in conditions of culture in minimal medium. By complementing said strains with a vector carrying an auxotrophic marker, the strains which correctly express this gene survive. The auxotrophic marker complements the deleted gene and allows the cell to survive in minimal medium. In a particular embodiment, the method according to the invention is based on this principle and a vector expressing an auxotrophic marker as a fusion protein with the library of gene variants encoding the protein of interest which one wants to improve will be used. Thus, if the fusion protein is correctly expressed, it will complement the deleted gene and allow the cell to survive when grown in non-complementing medium. Otherwise, the cell cannot survive.

Selection can be performed by using a parameter other than survival. Any reporter protein system stable in non-standard physicochemical conditions, known to those skilled in the art, can be used. In one embodiment, the protein Π is a mutant stable in non-standard physicochemical conditions, of a fluorescent or luminescent protein, for example GFP (green fluorescent protein). Several mutants tolerating temperatures slightly higher than wild type GFP are now available, and display different spectral characteristics (see for example: Siemering K R et al. Curr. Biol. 1996; 6:1653-63). With regard to stability at extreme pH, Enhanced GFP has been shown to undergo denaturation at acidic pH (pH 2) which is reversible when the medium is neutralized (pH 7) (Malik A et al. Anal. Biochem. 2005; 340:252-8). In an analogous manner, GFP variants or other fluorescent or luminescent proteins or enzymes whose product is fluorescent, which are stable and/or active in non-standard physicochemical conditions can be used in the method of the invention.

In a particular embodiment, the reporter protein is stable and possibly fluorescent in the chosen non-standard physicochemical conditions and it is fluorescent or luminescent in standard conditions. In particular, the reporter protein used can be non-fluorescent or non-luminescent in the non-standard physicochemical conditions where it is produced but it becomes fluorescent when it is placed in standard physicochemical conditions.

For example, it can be produced at high temperature, undergo a reversible denaturation and resume a conformation making it fluorescent or luminescent when it is placed at room temperature.

The cells containing proteins $P_i$ stable in non-standard physicochemical conditions correctly express the fusion protein $P_i$-Π and said cells fluoresce when they are excited at a suitable wavelength. Said cells can subsequently be sorted simply and rapidly, in standard conditions (in particular: at room temperature) by using a FACS (fluorescence activated cell sorter). It should be noted that, in this embodiment, for the selection to take place correctly, it is not absolutely necessary for the protein to fluoresce in the non-standard physicochemical conditions in which the chosen extremophilic microorganism grows and in which the fusion protein $P_i$-Π is expressed. In fact, all that is needed is that the reporter protein be stable, or, at the very worst, undergo a reversible denaturation, in the chosen non-standard physicochemical conditions, since it is the activity of said protein in standard conditions (in particular: at room temperature) which enables the selection.

In a particular embodiment, the cells of the extremophilic microorganism expressing the fusion proteins $P_i$-Π are cultured on solid medium and selection is performed simply by harvesting the fluorescent or luminescent colonies.

In another particular embodiment, the protein Π is a protein which, directly or indirectly, leads to the transformation of a substrate into a colored product. The selection then is preferably performed on solid medium by collecting colonies having the color of the colored product. The reporter protein is preferably a stable variant of beta-galactosidase.

Another thermostable reporter protein which can be used in the invention is the thermostable esterase of *A. acidocal-*

*darius* (Agafonov D E et al. FEBS Lett. 2005; 579:2082-86.). This article also describes a test allowing easy detection of said protein.

It is likely that many other proteins which can be used as selection markers in extremophilic microorganisms will be produced in the future. The method of the invention is not dependent on a particular protein Π.

Regardless of the nature of the protein Π, when the gene encoding the fusion protein $P_i$-Π is constructed, a certain number of conventional rules must be observed. For instance, the gene of interest and the gene encoding the reporter protein must be linked without interrupting the reading frame. Care must also be taken with respect to the steric constraints of the two proteins. This is because the fusion of the protein of interest with the reporter protein may prevent one or the other from adopting its natural conformation. Its structure would be modified, and its activity would disappear. To avoid this potential pitfall, it is generally desirable to add a sequence encoding a linker peptide between the gene encoding the protein of interest and that encoding the reporter protein. In general, said linker peptide has a structure as neutral as possible (i.e., generally with no secondary structure motif) and has no particular intrinsic activity. Typically it is composed of 8 or 9 neutral amino acids which must not affect the structure of the proteins and not be a target of proteases. Preferably it is flexible and hydrophilic (Sieber V. Methods Mol. Biol. 2003; 230:45-55; U.S. Pat. No. 6,448,087). The amino acids which form the linker peptide are preferably selected from the group consisting of Gly, Ser, Ala, Val and Thr. Classically, linker peptides are often formed by a motif of the type $(Gly_4\text{-}Ser)_x$, with x=3 for example. Of course the fragment coding for the linker peptide must be introduced in such a way that the reading frame is preserved over the entire sequence comprising the protein of interest, the linker peptide and the reporter protein. Two constructs are possible a priori for the fusion protein $P_i$-Π: either $P_i$ is located at the N-terminal end and Π at the C-terminal end, or vice versa. Generally, the construct wherein $P_i$ is upstream is preferred. In an alternative embodiment the opposite construct is used (protein Π located upstream).

A particular aspect of the invention concerns a fusion protein comprising a protein of interest or a variant thereof and a reporter protein which is stable in non-standard physicochemical conditions, as well as a nucleic acid or vector encoding said fusion protein. Preferably, the non-standard physicochemical conditions under consideration are high temperature. Thus, the reporter protein is thermostable. Preferably, the reporter protein is an antibiotic resistance protein stable in non-standard physicochemical conditions, and in particular a thermostable antibiotic resistance protein. In an especially preferred embodiment, the thermostable reporter protein is kanamycin nucleotidyltransferase or the bleomycin resistance protein.

The vector carrying the sequence encoding the fusion protein according to the invention comprises all the elements necessary for its expression in the chosen extremophilic host microorganism. It can also comprise elements allowing an expression in standard microorganisms. Of course it comprises the elements necessary for reproduction of the vector (eg., origin of replication). Preferably, the vector is a plasmid.

The choice of the extremophilic microorganism used for expression in step b) and selection in step c) depends on the chosen non-standard physicochemical condition, the ease of transformation and culture of the cells of said microorganism and the capacity of said microorganism's cellular machinery to correctly express the protein Π and the fusion proteins $P_i$-Π.

In particular the following are useful: thermophiles (which live at a temperature comprised between 60° C. and 80° C.), hyper-thermophiles (which live at temperatures above 80° C.), psychrophiles (which live at a temperature below 15° C.), halophiles (which live in the presence of high salt concentrations, for example 4M NaCl or 3M KCl), alkalophiles (which live at pH greater than 9), acidophiles (which live at pH less than 3), piezophiles (which live at pressures of up to 110 Mpa), metallophiles (which live in the presence of high concentrations of metals), radiophiles (which live in the presence of high levels of radiation), microaerophiles (which live in spite of low oxygen concentrations).

For example, and not by way of limitation, the extremophilic microorganism can be selected from the following:

*Thermus* sp (ATCC accession number: 27737; 31674; 43814; 43815; 27978);

*Thermus aquaticus* Brock and Freeze (ATCC accession number: 25104; 25105; 31558);

*Thermus thermophilus* Oshima and Imahori (ATCC accession number: 27634);

*Thermus filiformis* Hudson et al. (ATCC accession number: 43280);

*Themococus* sp (ATCC accession number: 55659);

*Alicyclobacillus acidocaldarius* (ATCC accession number: 27009);

*Sulfolobus solfataricus* Zillig et al. (ATCC accession number: 35091; 35092); and

*Haloferax mediterranei* (ATCC accession number: 33500) or halophilic bacteria from the family of *Halomonadaceae*.

In a preferred embodiment, the microorganism is thermophilic and preferably it is *Thermus thermophilus* or *Thermus aquaticus*.

As noted earlier, said same microorganisms can also be an interesting source of proteins Π.

An important problem may arise, depending on the sequence of the starting protein $P_0$: the problem of codon bias. In fact, extremophilic microorganisms have a very different codon usage than that of non-extremophilic cells, which are generally the source of the protein $P_0$. As a function of data on the heterologous expression of $P_0$ in the chosen extremophilic microorganism, it is possible that said difference in codon usage will prevent the correct expression of the fusion proteins $P_i$-Π in step b). It is then necessary to modify the sequence of the gene encoding $P_0$ in the expression vector prior to step a) so as to modify codon usage to make it compatible with expression in the extremophilic microorganism chosen in steps b) and c). When selection has been performed, it may again be necessary to modify the sequence of the gene encoding the improved (rendered stable) protein $P_i$ so that it can be expressed in the mesophilic microorganism subsequently used for production. For example, if the original protein originates from a mammal and if the microorganism used for selection is a thermophilic bacteria, one can first modify the codons of the corresponding gene to allow selection in a thermophile then again modify the "hit" sequence obtained from molecular evolution so that the improved protein can be produced in a classical production host, *Pischia pastoris* for example. In a preferred embodiment, the sequence of $P_0$ is only modified once, at the start, so that it can be correctly expressed in both the extremophilic microorganism used for the selection and the microorganism later used for production of the improved variants. In such case a set of "consensus" isocodons is used (synonymous codons, that is to say, coding for the same amino acid) which avoids the need for codons with low usage in the chosen microorganisms. The problem of different codon usage profiles is well known to those skilled in the art and it is encountered, with a more or less serious impact, in almost all cases of heterologous expression.

In a particular embodiment, the problems related to differences in codon usage can be resolved by re-writing, through site directed mutagenesis before step a), a small number of codons (typically: 1-20) particularly detrimental for the expression of $P_0$ (and libraries created from $P_0$) in the extremophilic microorganism chosen for the selection.

In another embodiment, said problems are resolved by completely re-synthesizing the gene encoding the protein $P_0$ by oligonucleotide concatemerization.

Scales such as the CAI (Codon Adaptation Index; Sharp P M et al. Nucleic Acids Res. 1987; 15:1281-95), and the use of dedicated software can guide the approach leading to the choice of sequence elements to be modified or of the sequence to be synthesized.

Indeed, for some proteins $P_0$, and according to the protein Π used, the expression of the $P_i$-Π library in an extremophilic microorganism will naturally take place at a level sufficient for selection, such that no codon re-writing will be necessary.

The library of variants of the protein of interest can be prepared either before fusion with the reporter protein or after said fusion. In a preferred embodiment of the invention, the method comprises in a first step preparing a vector carrying the sequence encoding the fusion protein comprising the protein of interest and the reporter protein, then generating the library of variants of the protein of interest.

The library of variants of the protein of interest can be generated by a mutagenesis technology. In a preferred embodiment, the library of variants of the protein of interest is created by Massive Mutagenesis® technology. It can also be created by another mutagenesis technology and in particular: random mutagenesis, site directed mutagenesis, saturation mutagenesis, elongation mutagenesis, in vivo mutagenesis.

In an alternative embodiment, it can be generated by an in vivo or in vitro genetic recombination method. Preferably, it is created by in vitro circular recombination (patent application FR0503364 filed by Biomethodes) of several natural or synthetic genes encoding thermostable or non-thermostable versions of said protein. However, it can also be created from recombination of several natural or synthetic genes encoding thermostable or non-thermostable versions of said protein by recombination technology and in particular: DNA-Shuffling®, StEP, in vivo recombination.

In another alternative embodiment, the library of variants of the protein of interest is created by direct cloning of nucleic acids from an environmental source using metagenomics technologies. The metagenomics approach used may be of the functional type, or the sequence-dependent type, or the SIGEX type.

Figure 3:
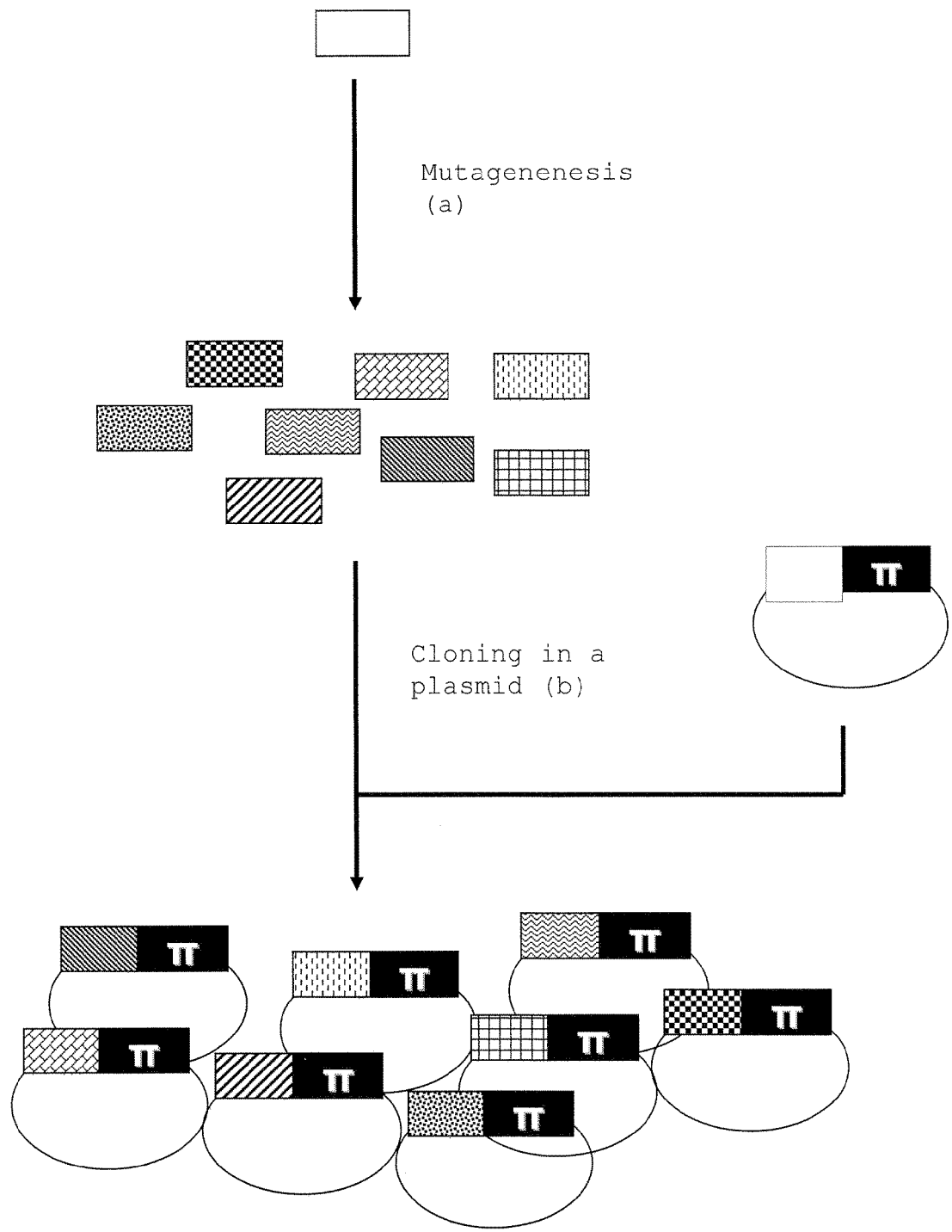
Figure 4:
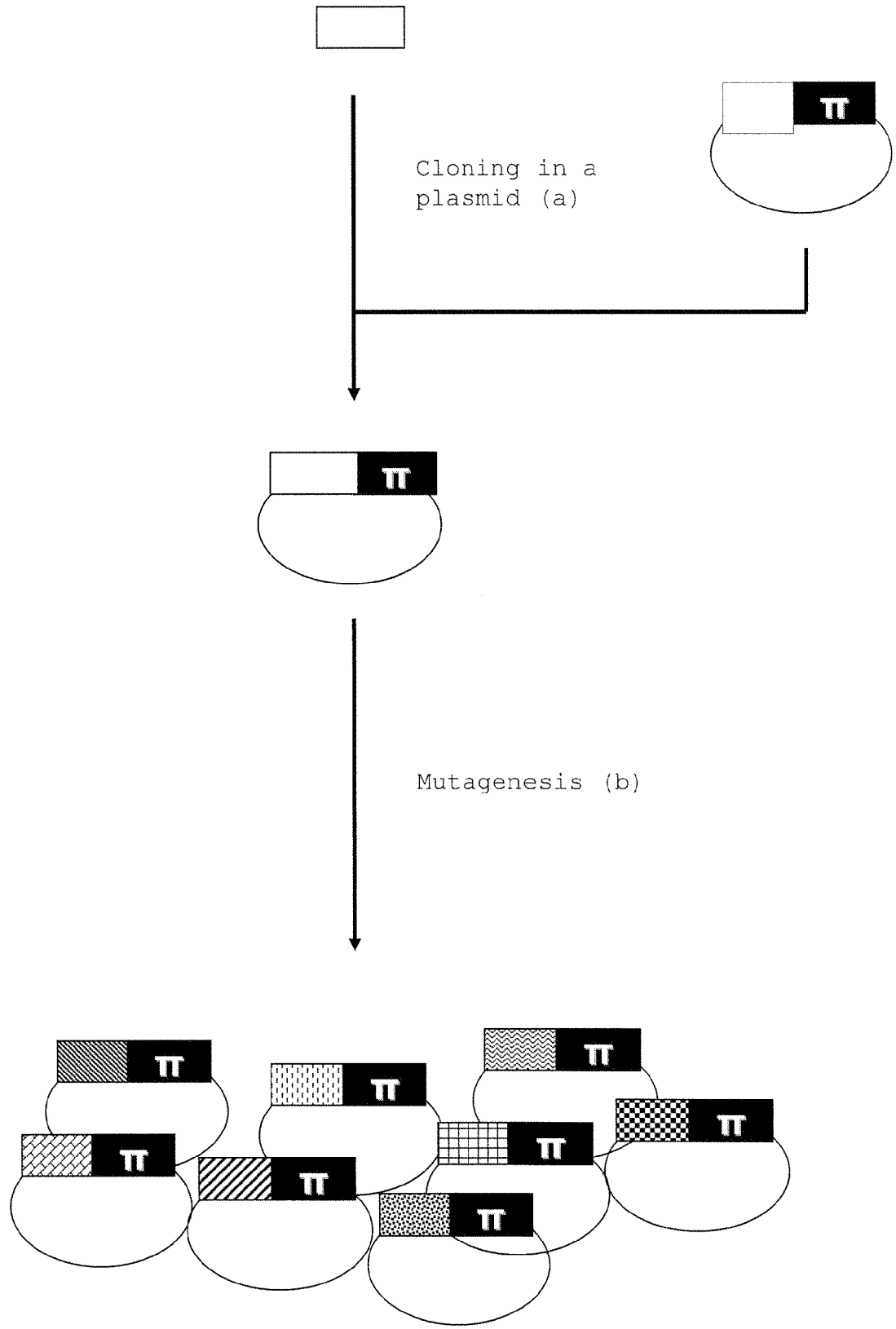
Figure 7:
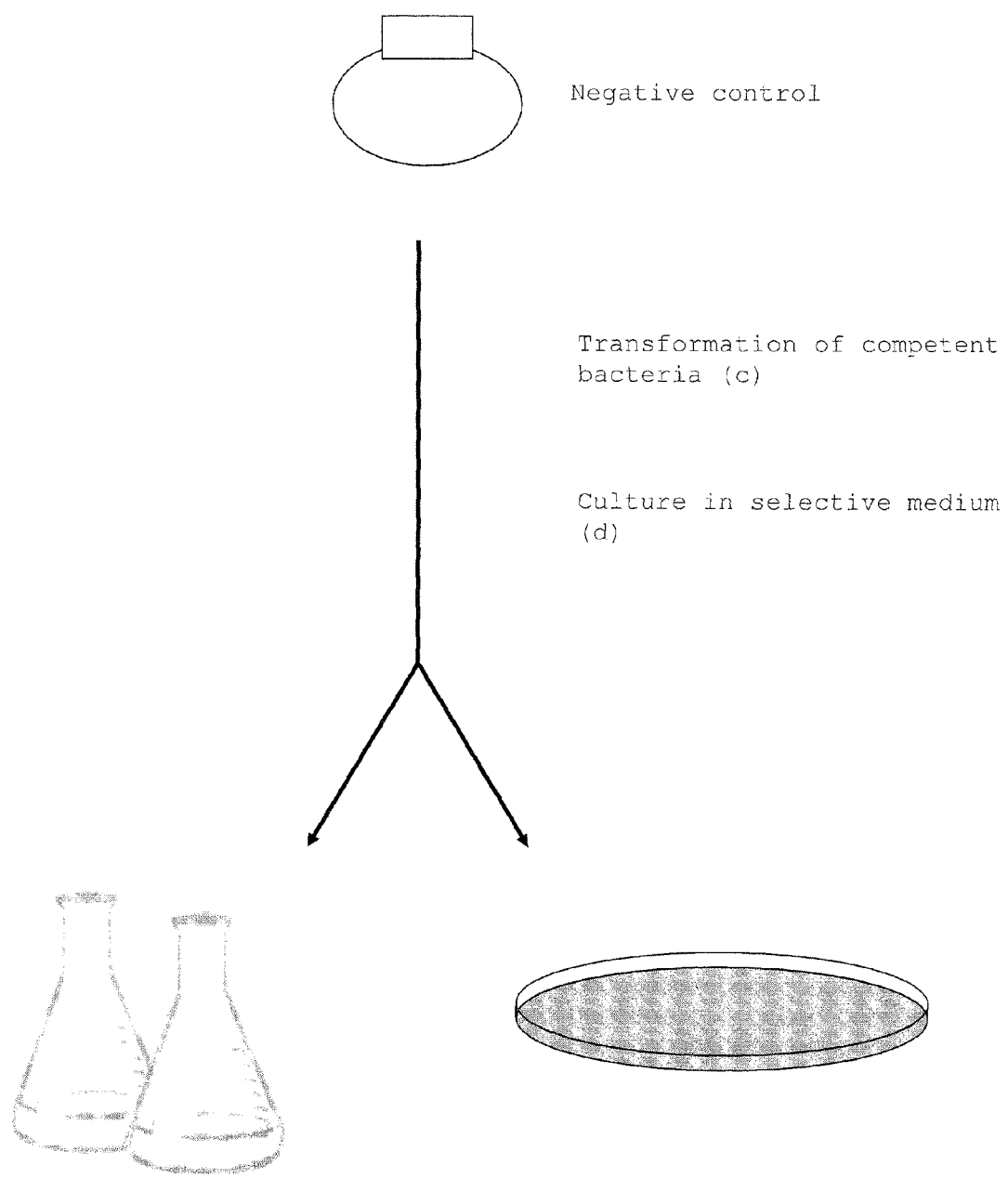

Embodiment 1: Mutagenesis and Selection by Survival of a Thermophile at High Temperature In a first embodiment, the method according to the invention is characterized by the use of mutagenesis, selection by survival (FIG. 5) and by the following sequence of steps:
a) Cloning of the gene encoding the protein of interest $P_0$ in a plasmid vector containing, in addition to the sequences necessary for its own replication and for its expression in a thermophilic microorganism, a gene encoding a protein Π conferring resistance to an antibiotic at high temperature. The plasmid also carries an *E. coli* origin of replication and a classical antibiotic resistance gene in *E. coli*. The gene encoding $P_0$ is cloned in-frame with the gene encoding protein Π, so as to obtain a fusion protein $P_0$-Π, either 5', or 3' (which corresponds to the two possible orientations of the fusion protein). Preferably, a sequence coding for a peptide linker is inserted between the protein of interest $P_0$ and the thermostable reporter protein Π so that the two proteins are far from each other and can fold without interference (FIGS. 1 and 2).
b) Generation, by a mutagenesis method and by using *E. Coli*, of a library of $P_i$ mutants (i=1, 2, . . . N where N is comprised between 2 and $10^{10}$, and preferably comprised between $10^3$ and $10^{10}$ or between $10^3$ and $10^8$) (FIGS. 3 and 4).
c) Transformation of the library obtained in step b) into a thermophilic microorganism.
d) Culturing, for a period of time necessary for growth of the microorganisms, for example for 30 minutes to 3 days, and preferably from 3 to 24 hours or 8 to 48 hours, in liquid or solid medium (FIG. 5 or FIG. 6), at high temperature (preferably: 50 to 100° C.), the cells of the thermophilic microorganism, in the presence of the thermostable antibiotic.
e) Preparation of plasmid DNA from the culture. Said DNA is enriched in genes encoding thermo stable variants of the protein of interest $P_0$.

In a particular embodiment, the sequence of the gene encoding the protein of interest $P_0$ is modified prior to step a), by substituting suitable isocodons.

In a particular embodiment, other isocodon substitutions are also introduced after step e) after molecular evolution in order to adapt to the codon usage of the microorganism subsequently chosen for production of the improved protein.

In a preferred embodiment, the mutagenesis method used is Massive Mutagenesis® technology.

In another embodiment, and with adaptations obvious to those skilled in the art, the mutagenesis method used is not Massive Mutagenesis® but random mutagenesis, site directed mutagenesis or elongation mutagenesis (Matsuura T et al. Nat. Biotechnol. 1999; 17:58-61), Adaptations are necessary in particular in the case where the mutagenesis method used does not work on circular DNA but on linear DNA. It should be noted that if one subclones in a vector already containing the gene encoding the protein $P_0$, there is a risk of obtaining false positives (religated plasmids without the insert).

In a particular embodiment, and with adaptations obvious to those skilled in the art, the mutagenesis is performed in vivo, by using mutator strains.

In a particular embodiment, the library of variants is created in step b) not in *E. coli*, but directly in a thermophilic microorganism.

In a preferred embodiment, the antibiotic used for the selection in the thermophilic microorganism is kanamycin, and the resistance gene used codes for thermostable kanamycin nucleotidyltransferase.

In a particular embodiment, the gene encoding a protein active at high temperature conferring antibiotic resistance does not code for kanamycin nucleotidyltransferase, but another protein Π active at high temperature conferring resistance to another antibiotic (itself thermostable).

In a particular embodiment, and with adaptations obvious to those skilled in the art, the selection by survival at high temperature is performed not by using an antibiotic, but by using an auxotrophic strain, in particular an auxotrophic thermophilic strain, the reporter gene in this case re-establishing the ability of the strain to grow on minimal medium.

Embodiment 2: Recombination and Selection by Survival of a Thermophile at High Temperature In a second embodiment, the method according to the invention is characterized by the use of recombination, selection by survival (FIG. 5) and by the following sequence of steps:
a) Choice of 2 to 100 (preferably 2 to 10) non-thermophilic or thermophilic microorganisms whose genomes code for different variants of the protein of interest $P_0$. Said variants differ in terms of their activity and their thermostability. This embodiment allows to recombine the corresponding genes then to select the novel genes thus created so as to improve the activity of the protein of interest at high temperature.
b) Cloning of the genes encoding the 2 to 100 (preferably 2 to 10) proteins $P_i$, all in the same plasmid vector which, in addition to the elements necessary for its own replication in a thermophile (or a hyper-thermophile) and in $E.$ $Coli$, also contains an ampicillin resistance gene allowing the selection of transformed clones, and a gene encoding a reporter protein Π active at high temperature which confers resistance to an antibiotic, itself stable at high temperature. The genes encoding $P_i$ are cloned in frame with protein Π, so as to obtain fusion proteins $P_i$-Π. Preferably, the genes encoding $P_i$ are all placed 5' to the coding gene. Alternatively, they can all be placed 3' (which corresponds to the two possible orientations of the fusion protein). Preferably, a sequence coding for a peptide linker is inserted between the protein of interest $P_i$ and the reporter protein Π so that the two proteins are far from each other and can fold without interference.
c) Recombination, by a genetic recombination method (i.e., in vivo or in vitro, homologous or sequence-independent, random or site directed), of the genes $P_i$ which leads to the creation of a library.
d) Transformation of the library obtained in step c) into a thermophilic microorganism.
e) Culturing, for a period of time necessary for growth of the microorganisms, for example for 30 minutes to 3 days or 3 to 24 hours, and preferably 8 to 48 hours, in liquid or solid medium, at high temperature (preferably: 50 to 100° C.), the cells of the thermophilic microorganism used, in the presence of a suitable concentration of thermostable antibiotic.
e) Preparation of plasmid DNA from the culture of step e). Said DNA is enriched in genes encoding thermostable variants of the protein of interest $P_0$.

In a particular embodiment, the sequence of the genes encoding the protein $P_i$ is modified after step a) and before step b), by suitable synonymous mutations introduced by site directed mutagenesis or by resynthesizing the gene so as to adapt to the codon usage in the chosen thermophilic microorganism.

In a particular embodiment, other suitable synonymous mutations are also introduced after molecular evolution in order to adapt to the codon usage of the microorganism subsequently chosen for production of the improved protein.

In a particular embodiment, the recombination is performed by using the in vitro circular recombination method (patent application FR0503364 filed by Biomethodes).

In a particular embodiment, and with adaptations obvious to those skilled in the art, the recombination method used is not in vitro circular recombination but DNA Shuffling® (Stemmer W P. Nature. 1994; 370:389-91), StEP (Zhao H. Methods Enzymol. 2004; 388:42-9) or any other suitable homologous or sequence-independent recombination method. Adaptations are necessary in particular in the case where the recombination method used does not work on circular DNA but on linear DNA.

In a particular embodiment, and with adaptations obvious to those skilled in the art, the recombination is performed in vivo.

In a preferred embodiment, the antibiotic used for the selection in the thermophilic microorganism is kanamycin, and the resistance gene used codes for thermostable kanamycin nucleotidyltransferase.

In a particular embodiment, the gene encoding a protein active at high temperature conferring antibiotic resistance codes for another protein Π active at high temperature conferring resistance to another antibiotic (itself thermostable).

In a particular embodiment, and with adaptations obvious to those skilled in the art, the selection by survival is performed not by using an antibiotic, but by using an auxotrophic strain, in particular an auxotrophic thermophilic strain, the reporter gene in this case re-establishing the ability of the strain to grow on minimal medium.

Embodiment 3: Metagenomics Technology and Selection by Survival of a Thermophile at High Temperature In a third embodiment, the method according to the invention is characterized by the use of metagenomics technology, and by the following sequence of steps:
a) Choice of an environmental source of DNA, for example, and obviously not by way of limitation, seawater and in particular water from the ocean ridges, soil, and in particular the rhizosphere, the air, the Antarctic ice, etc.
b) Starting from the DNA extracted from said environmental source, direct cloning by metagenomics technology (Streit W R et al. Curr. Opin. Biotechnol. 2004; 15:285-90; Daniels R Curr. Opin. Biotechnol. 2004; 15:199-204), according to the method of sequence-dependent screening, functional screening or else SIGEX ("substrate-induced gene-expression screening") (Yun J et al. Microb. Cell Fact. 2005; 4:8) of an indeterminate number of variants $P_i$ of a protein of interest $P_0$ in a same plasmid vector containing, in addition to all the elements necessary for its own replication and expression (in a thermophile or hyper-thermophile and also in a mesophile), a gene encoding a thermostable reporter protein Π which confers resistance to an antibiotic (itself thermostable). The genes encoding $P_i$ are cloned in frame with protein Π, so as to obtain a fusion protein $P_i$-Π. A library is generated. Either the genes encoding $P_i$ are all placed 5' of the coding gene, or they are all placed 3' (which corresponds to the two possible orientations of the fusion protein). Preferably, a sequence coding for a peptide linker is inserted between the protein of interest $P_i$ and the thermostable protein Π so that the two proteins are far from each other and can fold without interference.
c) Transformation of the library obtained in step b) into the thermophilic microorganism used for selection.
d) Culturing, for a period of time necessary for growth of the microorganisms, for example for 30 minutes to 3 days or 3 to 24 hours, and preferably 8 to 48 hours, in liquid or solid medium, at high temperature (preferably: 50 to 100° C.), the cells of the thermophilic selection microorganism, in the presence of a suitable concentration of thermostable antibiotic.

e) Preparation of plasmid DNA from the culture. With respect to the initial library, this DNA is enriched in genes encoding thermostable $P_i$ proteins.

In a particular embodiment, suitable synonymous mutations are also introduced after molecular evolution in order to adapt to the codon usage of the microorganism subsequently chosen for production of the improved protein.

In a preferred embodiment, the antibiotic used for the selection in the thermophilic microorganism is kanamycin, and the resistance gene used codes for thermostable kanamycin nucleotidyltransferase.

In a particular embodiment, the gene encoding a protein active at high temperature conferring antibiotic resistance codes for another protein Π active at high temperature conferring resistance to another antibiotic (itself thermostable).

In a particular embodiment, and with adaptations obvious to those skilled in the art, the selection by survival is performed not by using an antibiotic, but by using an auxotrophic strain, in particular an auxotrophic thermophilic strain, the reporter gene in this case re-establishing the ability of the strain to grow on minimal medium.

Embodiment 4: Screening by FACS

In a fourth embodiment, the method according to the invention is characterized by the use of a fluorescent protein Π which is stable in non-standard physicochemical conditions. The protein can be directly active in said non-standard physicochemical conditions; alternatively, it can be produced in said non-standard physicochemical conditions without being active, then become active when it is placed in standard conditions.

Sorting takes place using flow cytometry and a FACS (fluorescence activated cell sorter; FIG. 9). This embodiment is closer to high-throughput screening than to selection, since the cells are sorted one by one. However the throughput is fairly similar to the case of selection by survival: typically $10^2$ to $10^4$ cells sorted per second by FACS, or the possibility of screening libraries of about $10^7$ variants in one hour.

In this fourth embodiment, the method according to the invention is characterized by the following sequence of steps:
a) Construction of a library of plasmids containing all the elements necessary for their replication and expression (in an extremophile as well as in the mesophile optionally used to generate diversity at the beginning or for production of the improved protein at the end), and containing a sequence coding for a fusion protein $P_i$-Π, where $P_i$ is a variant of the protein of interest (said variants being obtained by mutagenesis, recombination or else metagenomics technologies) and where Π is a fluorescent or luminescent protein (for example, GFP or a variant of GFP). Preferably the fusion protein includes a suitable peptide linker. It is essential that the protein Π used is not only stable at high temperature but can be produced by expression at high temperature in a thermophilic microorganism (FIG. 1).
b) Transformation of an extremophilic microorganism with a plasmid library (FIGS. 3 and 4).
c) Expression of the library in non-standard physicochemical conditions (for example, depending on the extremophile, at a temperature of 75° C., or at a concentration of 3M NaCl, or at pH 2).
d) Sorting, at low temperature (preferably, from 5° C. to 45° C.) and by using a FACS, or a miniaturized FACS (µFACS), or else several µFACS used in parallel mode, of the cells of the extremophilic microorganism. The fraction of cells which emit a fluorescence above an empirically determined threshold, when excited at a suitable wavelength, is collected (for example, the 0.1% of cells with the most fluorescence is collected).
e) Preparation of the plasmid DNA from said cells. With respect to the initial bank, said DNA is enriched in genes encoding thermostable proteins.

In a particular embodiment, site directed mutagenesis or gene synthesis is used to produce the isocodon substitutions necessary for good heterologous expression.

Figure 8:
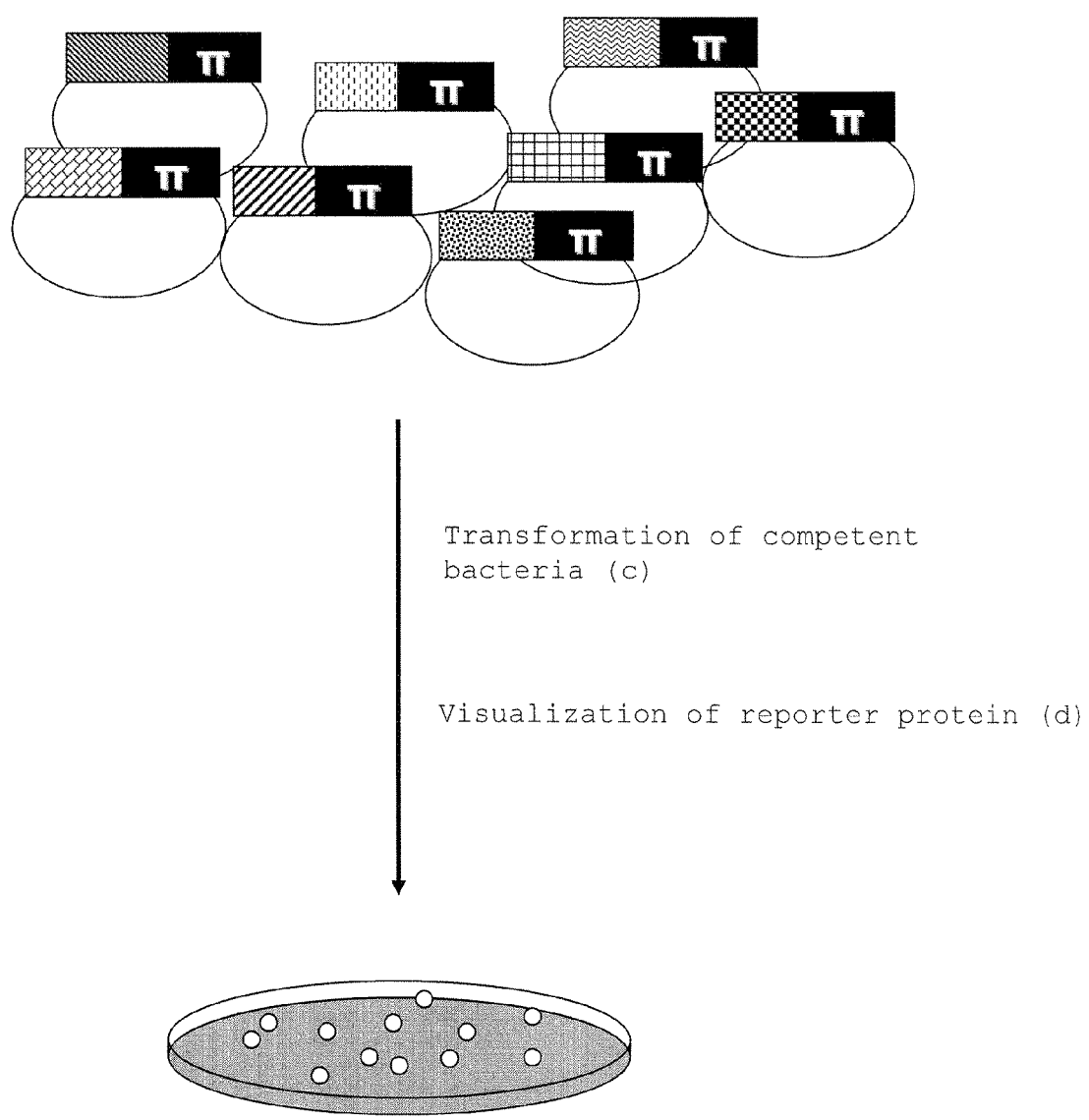

In a particular embodiment, the selection does not take place by FACS, but by reading the fluorescence of colonies grown on a solid support then harvesting and subcloning colonies displaying a high fluorescence (FIG. 8).

EXAMPLES

Example 1: Example of a Plasmid

A plasmid usable in the method according to the invention contains the following elements, in a correct order and so that only a single reading frame is used:
a) an origin of replication in an extremophile (used for the selection), and optionally another origin of replication in a mesophile (optionally used to generate genetic diversity or for production of the improved protein);
b) one or more promoters, optionally one or more promoters allowing conditional expression;
c) a resistance gene to ampicillin or to another classical antibiotic, under the control of a suitable promoter, which allows the selection of transformants in *E. coli* or any other suitable classical system (for example, if yeasts are used, said gene is preferably an auxotrophic marker);
d) a gene encoding a reporter protein stable in non-standard physicochemical conditions and possibly active in said conditions;
e) optionally, a sequence fragment coding for a linker peptide of about ten amino acids;
f) a gene encoding the protein of interest or a variant thereof.

Example 2: Improving the Thermostability of a Phytase

Increasing the thermostability of bacterial phytases would resolve a major environmental and economic issue in the field of animal feed. *Escherichia coli* phytase (myo-inositol hexakisphosphate phosphohydrolase, EC 3.1.3.8), catalyses the cleavage of phytic acid, the major form of phosphorus storage in plant seeds, releasing a phosphomonoester. The phosphorus present in phytic acid is virtually unusable by monogastric animals such as swine and fowl. Therefore, supplementing the feed of said animals with a phytase increases the nutritional value of the feed. By reducing the need for inorganic phosphorus supplements in animal feed, phytases also help to preserve the environment. The manufacturing processes for animal pellets or other feeds generally involve steps carried out at high temperature (typically: a short phase of 1 second to 3 minutes, at 80° C. or higher). A phytase is therefore needed which is stable at these high temperatures, all while being active at body temperature if the aim is to incorporate it into animal feed.
a) The PhyA gene encoding *Escherichia coli* phytase is cloned in frame with the gene encoding thermostable kanamycin nucleotidyltransferase. A sequence coding for a linker peptide of about ten amino acids is inserted between the two genes. The vector also contains an ampicillin resistance gene (non-thermostable) under the control of a bacterial promoter, and all the elements necessary for replication in *T. thermophilus* and *E. coli*.

b) By using suitable oligonucleotides, high-throughput site directed Massive Mutagenesis® technology is used on the plasmid containing the construct of step a) to generate a library of variants of the PhyA gene.

c) A thermophilic microorganism (*Thermus thermophilus*) is transformed with the plasmid containing the library of PhyA gene variants obtained in step b).

d) The thermophilic microorganism is cultured, for several hours, at a temperature of 70° C., in the presence of a suitable concentration of kanamycin. After 48 hours of growth in liquid medium, growth of the bacteria is significantly higher than in the group transformed by the non-mutant plasmid, used here as control.

e) Plasmid DNA is prepared from the cells cultivated in step d).

f) *E. coli* is transformed with said plasmid DNA and plated on a petri dish containing ampicillin.

g) The dish is left overnight, then individual colonies taken from the petri dish of step f) are subcloned into about ten 96-well microplates.

h) Conditions allowing expression of the phytase in *E. coli* are used, after first confirming that the activity of said phytase is not altered by the presence of the fused reporter gene.

i) The bacterial cells are lysed.

j) A suitable test is used to rapidly screen the clones expressing a phytase which, in addition to having acquired thermostability, is active at low temperature (37° C.).

In a particular embodiment, phytase activity is directly measured in the culture supernatant. To this end, 20 µl of culture supernatant are incubated with 200 µl of sodium phytate solution (10 g/l in buffer containing 250 mM sodium acetate-1 mM $CaCl_2$-pH 5.5) at 37° C. for different times (from 15 min to 18 h). At t=0 and at the end of the reaction, 50 µl of reaction mix are removed and mixed with 50 µl of 20% TCA to stop the reaction. Phytase activity is measured by assaying free phosphates in the reaction medium. This assay is performed by adding 100 µl of a 4:1 mixture of 12 mM ammonium molybdate and 380 mM iron sulfate. After a 30 min incubation at 20° C. (room temperature), OD is measured at 620 nm. The signal induction factor is calculated by the ratio (final OD)/(initial OD).

Example 3: Improving the Resistance of a Cellulase to Extreme pH

Cellulases can be used in biomass conversion but also in various industrial processes, including food processing, textiles, detergents and paper. In view of a use in several of these processes, it would be desirable to have a cellulase with a high specific activity at neutral or alkaline pH (pH 6 to pH 11). In a recent report (Wang T et al. Biomol. Eng. 2005; 22: 89-94), directed evolution was used to obtain a cellulase variant, endoglucanase III (EG III) from *Trichoderma reesei*, having a pH optimum (5.4) which is 0.6 units higher than the wild type enzyme. Efforts are being made to take this improvement even further. In the case of a cellobiohydrolase from glycosyl hydrolase family 7 (Cel7), a very clear correlation has been shown between thermostability and activity at alkaline pH (Boer H et al. Eur. J. Biochem. 2003; 270: 841-848).

a) The Cel7 gene encoding cellulase Cel7 from *Trichoderma reesei* is cloned in frame with the gene encoding thermostable kanamycin nucleotidyltransferase. A sequence coding for a linker peptide of about ten amino acids is inserted between the two genes.

b) By using suitable oligonucleotides, high-throughput site directed Massive Mutagenesis® technology is used on the plasmid containing the construct of step a) to generate a library of variants of the Cel7 gene.

c) A thermophilic microorganism (*Thermus thermophilus*) is transformed with the plasmid containing the library obtained in step b).

d) The thermophilic microorganism is cultured, for several hours, at a temperature of 70° C., in the presence of a suitable concentration of kanamycin.

e) Plasmid DNA is prepared from the cells cultivated in step d).

f) The plasmids obtained are cleaved around the gene of interest and the insert is subcloned into a plasmid allowing it to be expressed in *E. coli*. Said plasmid contains a tetracycline resistance gene. This subcloning makes it possible to bypass the presence of the fused reporter gene, which may interfere with the activity of the protein and therefore prevent the functional characterization of the more stable mutants obtained in the previous steps.

g) *E. coli* is transformed with said plasmid DNA and plated on a petri dish containing tetracycline.

h) The dish is left overnight, then individual colonies taken from the petri dish of step f) are subcloned into about ten 96-well microplates.

i) Conditions allowing expression of the cellulase in *E. Coli* are used.

j) The bacterial cells are lysed.

k) A suitable test is used to rapidly screen the cellulases having a high specific activity at alkaline pH, in order to isolate those which conserved a significant level of activity among these mutants associated with an increased stability.

Example 4: Improving the In Vivo Stability of a Cytokine a) The IL7 gene is used, encoding a cytokine which has potential as a human therapeutic protein and whose target parameter for improvement is its in vivo stability in the human body. The approach is based on identifying more highly thermostable mutants by using the method according to the invention, and in the hope that a significant fraction of said thermostable mutants will also be more resistant to proteolysis, and will also have a longer half-life in less stringent conditions, as previously described in the literature. Said gene is completely synthesized (with the overlap PCR method by assembling long, chemically synthesized oligonucleotides of about a hundred bases) with modification of the sequence of the human gene so as to obtain isocodon substitutions allowing it to be correctly expressed in *Thermus thermophilus* and in *E. coli*. Said resynthesized gene is cloned in frame with the gene encoding thermostable kanamycin nucleotidyltransferase. A sequence coding for a linker peptide of about ten amino acids is inserted between the two genes.

b) By using suitable oligonucleotides, high-throughput site directed Massive Mutagenesis® technology is used on the plasmid containing the construct of step a) to generate a library of variants of the IL7 gene.

c) A thermophilic microorganism (*Thermus thermophilus*) is transformed with the plasmid containing the library obtained in step b).

d) The thermophilic microorganism is cultured, for several hours, at a temperature of 70° C., in the presence of a suitable concentration of kanamycin.
e) Plasmid DNA is prepared from the cells cultivated in step d).
f) E. coli is transformed with said plasmid DNA and plated on a petri dish containing ampicillin.
g) The dish is left overnight, then individual colonies taken from the petri dish of step t) are subcloned into about ten 96-well microplates.
h) Conditions allowing expression of the cytokine in E. coli are used.
i) The bacterial cells are lysed.
j) A suitable test is used to rapidly screen the clones expressing a cytokine having a high specific activity at 37° C., after making sure that the presence of the fused reporter gene does not alter the activity of IL7.
k) A second screening on a smaller number of clones selected in step i) is performed using the parameter of plasma half-life of the cytokine.

Example 5: Generation of a Halotolerant Enzyme Using a Halophile a) One starts with a library of variants of a gene encoding an enzyme originating from a mesophilic microorganism, which is active in aqueous medium but has little or no activity at very high concentrations of a saline substrate, the conditions in which it is to be used (which is a classical problem in the field of biocatalysis). One way to achieve this is to improve the salt tolerance of said enzyme, by using a halophilic bacteria from the family of *Halomonadacea* (Halomonas, Chromohalobacter, Zymobacter), which can be genetically engineered (Vargas, C et al. J. Methods Mol. Biol. 2004; 267:183-208). Said gene library is cloned in frame with a plasmid allowing it to be expressed as a fusion protein with a reporter protein conferring resistance to an antibiotic, said reporter protein being stable and active in the conditions of life of the halophile. The plasmid also contains an E. coli origin of replication and an E. coli ampicillin resistance gene.
b) The halophilic microorganism is transformed with the construct of step a) and cultured, in the halophile's life conditions (therefore: in the presence of a high or even saturating concentration of one or more salts), in the presence of the antibiotic and in conditions allowing the fusion protein library to be expressed. A solid medium or a liquid medium may be used.
c) Plasmid DNA is prepared from the clones which grew.
d) E. coli is transformed with said plasmid DNA and plated on a petri dish containing ampicillin.
e) The dish is left overnight, then individual colonies taken from the petri dish of step d) are subcloned into about ten 96-well microplates.
f) Conditions allowing expression of the enzyme in E. coli are used.
g) The bacterial cells are lysed.
h) A suitable test is used to rapidly screen the clones expressing an active enzyme using the substrate of interest, after making sure that the presence of the fused reporter gene does not alter the activity of the enzyme of interest.

Example 6: Improving the Stability of a Cytokine: Production of Thermostable Mutants of Gamma Interferon By using a thermostable mutant of kanamycin nucleotidyltransferase (KNTase) as selection marker (Liao H H Enzyme Microb. Technol. 1993; 15:286-92; Sakon J et al. Biochemistry. 1993; 32: 11977-84) and *Thermus thermophilus* strain HB27 (whose optimal growth temperature is around 70° C.) as selection host, thermostable mutants of gamma interferon (IFNγ) were rapidly identified.

First, an E. coli/T. thermophilus shuttle vector was prepared. The human IFNγ gene was cloned into this vector in frame with the selection marker. A library of mutants was generated using Massive Mutagenesis® technology. Mutants were identified by the parameter of resistance to a high kanamycin concentration. Mutations were identified by sequencing. The mutations were then introduced into a mammalian expression vector allowing IFNγ production, and the improvement in thermostability was validated in a cell culture model.

Construction of an E. coli/T. thermophilus Shuttle Vector

Figure 10:
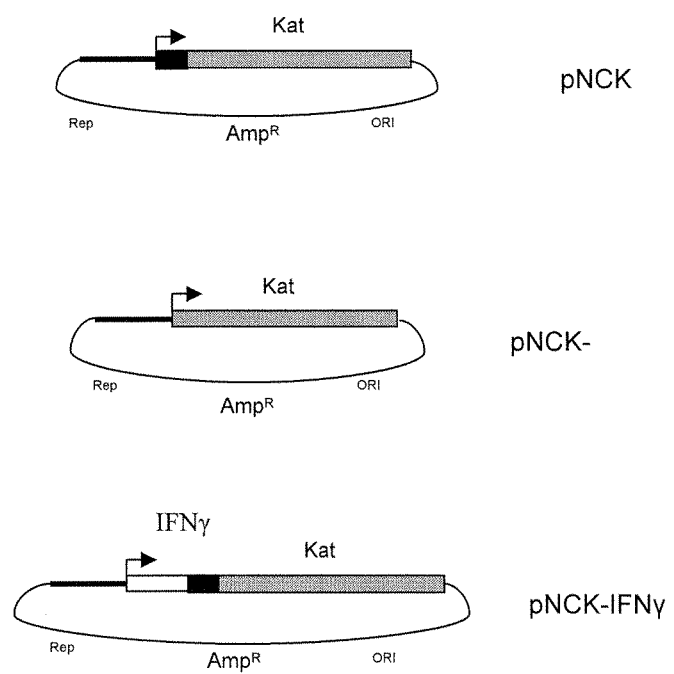

A pNCK vector was used, containing the E. coli and T. thermophilus origins of replication, an ampicillin resistance gene allowing selection of transformants in E. coli, and a gene encoding thermostable KNTase under the control of a promoter active in both E. coli and T. thermophilus (the ps1pA promoter) (FIG. 10). The nucleotide sequence of IFNγ (SEQ ID No. 5 coding for the mature form of 146 amino acids SEQ ID No. 6) was cloned between the NcoI and NotI sites of the pNCK vector at the N-terminal of KNTase (pNCK-IFNγ). The fused IFNγ and KNTase sequences were separated by a sequence coding for a linker peptide having the peptide sequence AAAGSSGSI (SEQ ID No. 8) and coded by the nucleic acid sequence GCG-GCC-GCA-GGA-AGC-TCT-GGT-TCC-ATC (SEQ ID No. 7).

Preparation of the Selection System

Two thermostable mutants described in the bibliography were also constructed and used as positive controls. They code for:
  the protein IFNγ E30C/S92C (Waschutza et al., 1996)
  the protein IFNγ Δ10 (C-terminal end of the protein deleted of the last 10 amino acids (Slodowski et al., 1991).

A negative control was also used; this mutant has a stop codon 30 base pairs before the end of the IFNγ sequence.

These different constructs were then transformed into T. thermophilus. The following were also transformed in parallel:
  the empty pNCK plasmid (positive control 1=KNTase under control of the ps1pA promoter and with the linker located in N-terminal)
  the pNCK-plasmid (positive control 2=KNTase under control of the ps1pA promoter but without the peptide linker)

T. thermophilus was transformed at 70° C. (by natural competence) with equivalent amounts of each plasmid. After a 4 hour incubation, 10 μl of a $10^{-3}$ dilution of the transformation mix were spotted on dishes containing different concentrations of kanamycin and incubated at 60° C. and 70° C.

Figure 11:
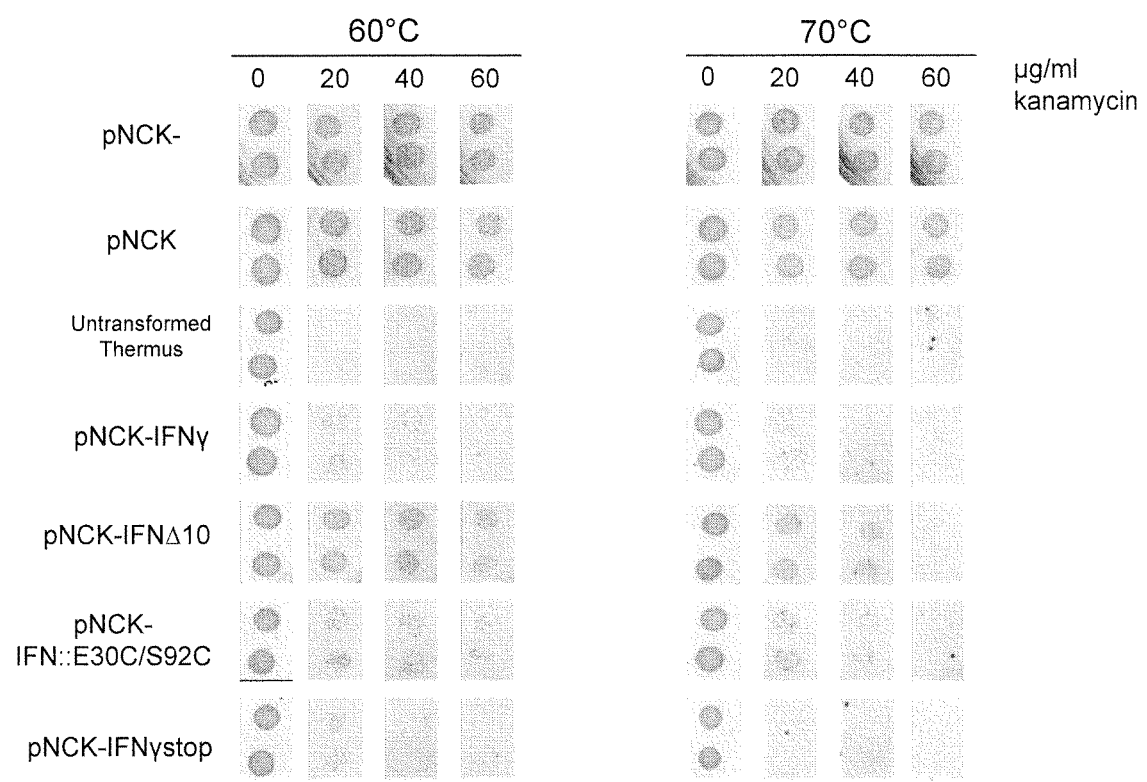

The results, presented in FIG. 11, show the growth of the different transformants after 48 hours of incubation at the two temperatures. It can be seen that:
  the untransformed strain only grew in the absence of kanamycin;
  the pNCK and pNCK-positive controls displayed a very high resistance;
  transformation with the pNCK-IFNγ plasmid conferred some resistance to the transformed strain;
  the different controls behaved as expected:
  the mutant with a stop codon (negative control) gave almost no signal;

the mutants described as thermostable were more resistant to kanamycin than pNCK-IFNγ at high temperature.

It is therefore possible to discriminate IFNγ variants with varying degrees of thermostability, thanks to the fusion thereof with thermostable KNTase and transformation in *T. thermophilus*. Moreover, the observed range of resistance defines the conditions for selecting more stable variants contained in a library of pNCK-IFNγ variants (20 to 40 µg/ml at 70° C.).

Generation of a Mutant Library

A library of IFNγ variants cloned in the pNCK vector was generated by using Massive Mutagenesis® technology. Total diversity was introduced on all positions located between 21 and 166. The mutant library potentially contains all the 2800 single mutants, a significant fraction of the 4 million double mutants, as well as mutants harboring three or more mutations.

Selection of Thermostable Mutants of IFNγ

The library was then transformed by natural competence at high temperature (70° C.) into *T. thermophilus* and selected at a kanamycin concentration of 20 or 40 µg/ml.

The different mutants isolated through this first selection were then retransformed into *T. thermophilus* and their level of resistance was compared with that of the wild type construct. In this manner 20 mutants, conferring more or less resistance but always greater than wild type, were confirmed. A thermostability factor (TF) was calculated for these 20 mutants, by dividing the number of clones obtained in selective conditions (20 or 40 µg/ml kanamycin and 70° C.) by the number of clones obtained in non-selective conditions (20 µg/ml and 60° C.), this in order to avoid any potential bias stemming from the transformation efficiency of each clone. It was seen that mutants which were selected at low stringency were associated with a lower thermostability factor than mutants selected at high stringency.

35 mutations were identified by sequencing the 20 clones: C21G, C21W, Y22D, Y22S, Y22T, Q24A, D25V, P26D, V28C, T50Y, W59F, S63R, Y76D, E98K, M100N, K109C, T119P, T119Y, Y121T, S122H, S122P, K131I, M140P, A147E, A147F, L158W, F159C, R162D, R162E, R162Q, R163G, R163T, R163L, A164E, S165V, The sequences of these mutants is given in FIG. 12 together with the corresponding thermostability factors.

Validation of IFNγ Mutant Stability in Mammalian Cells

Some of the 35 single mutations previously identified were separately cloned into the pORF/IFNγ vector (Invivogen), allowing transient expression of IFNγ in mammalian cells with the aid of a hybrid promoter (EF-1α-HLTV) and a SV40 strong polyadenylation signal.

COS7 cells were transfected in 24-well plates seeded at 30,000 to 60,000 cells per well when the cells reached 70-80% confluence. Transfection was performed for 30 minutes at room temperature with approximately 50 ng of DNA and Jet-PEI (Polyplus transfection) at a Jet-PEI/DNA ratio equal to 5. After 24 hours of transfection, the medium (500 µl IMDM+FCS+antibiotics) was replaced. Supernatants containing IFNγ (with a level of expression of approximately 0.5 to 1 µg/ml) were collected 24 hours post-transfection, aliquoted and stored at −20° C. before assaying IFNγ activity.

IFNγ is already known to specifically activate IFNγ receptors present on HeLa cells. IFNγ stimulates the Jak/Stat1 pathway in HeLa cells, resulting in particular in the transcriptional activation of genes under the control of promoters containing GAS (Gamma Activated Site) sequences. It is therefore possible to measure and compare the activities of IFNγ variants by transfecting into HeLa cells a reporter gene system in which luciferase (firefly luciferase) is cloned downstream of a promoter containing several GAS sites (pGAS/Luciferase promoter from Stratagene).

HeLa cells at 50-80% confluence were transfected in 96-well microplates according to the manufacturer's protocol: 20,000 cells per well were transfected with approximately 150 ng of pGAS/Luciferase DNA and Jet-PET at a Jet PEI/DNA ratio equal to 5. The mixture was vortexed for 30 seconds and left at room temperature for 30 minutes, Twenty microliters of the DNA/Jet-PEI mixture were then aliquoted into each well of the plate and the cells so transfected were grown for 24 hours at 37° C. in a 5% $CO_2$ atmosphere.

All cell culture reagents were from Invitrogen. HeLa and COS-7 cells were cultured in standard conditions (37° C. in a humid atmosphere containing 5% $CO_2$) using Dulbecco's Modified Eagle's Medium (D-MEM) and Iscove's Modified Dulbecco's Medium (IMDM), respectively. All these culture media contain an analog of L-glutamine (glutamax) and are supplemented with decomplemented fetal calf serum (10% final) and antibiotic concentrations: penicillin 100 U/ml and streptomycin 0.1 mg/ml. The pSV-Betagal™ vector (Promega), which expresses beta-galactosidase under the control of the SV40 early promoter, was used to normalize all transfection efficiencies.

The supernatants of COS7 cells transfected with the IFNγ mutants were then allowed to act on the transfected HeLa cells: the supernatants of IFNγ-containing COS7 cells were diluted 1:100. Ten microliters of said dilutions of COS7 cell supernatants containing IFNγ were added on HeLa cells transfected with pGAS/Luciferase. After 16 hours at 37° C., 5% $CO_2$ during which cytoplasmic expression of firefly luciferase took place, the cell pellets were collected and frozen. Fifty microliters of Glo Lysis Buffer™ (Promega) were added to lyse the cells. Lysis was carried out for 10 minutes with shaking at room temperature so as to release luciferase produced in response to specific stimulation by IFNγ. The actual test of luciferase activity was initiated by addition of the Bright Glo™ reagent (Promega) and the amount of luciferase which accumulated was then counted in a luminometer (FLX 800, Bio-Tek Instrument).

The total activity of each variant (relative to the wild type protein) was calculated as a mean of the results obtained in five different experiments (each at least in duplicate) and on culture supernatants from at least two different transfections. Error bars were calculated by the standard error of the mean (s.e.m). One way to present the total activity data is to report the basal activity of each variant as a percentage of the basal activity of non-mutated IFNγ expressed in the same conditions, for each transfection (FIG. 13). A portion of the mutants retained an activity equivalent or similar to that of wild type IFNγ.

Determination of Level of Activity and Level of Thermostability

COS7 cell supernatants were subjected to thermal denaturation (10 minutes at 59° C.). The activity induced by the non-denatured protein was then compared with the activity induced by said same denatured protein and the residual activity after heat denaturation was calculated for the protein under study (Residual activity=denatured activity/non-denatured activity*100). These values represent the mean of five different experiments (each at least in duplicate). Error bars were calculated by the standard error of the mean (s.e.m).

Thermostability and activity data with respect to non-mutant IFNγ are shown in FIG. 14. Some mutants had a residual activity much higher than that of wild type IFN. In particular, all the mutations identified on the single mutants in the initial screening showed this gain in residual activity. Only a fraction of the mutations identified on multiple mutants in the initial screening showed this improvement in residual activity. In the majority of cases, the improvement in thermostability can be considered to be conveyed by a single one of the several mutations in these multiple mutants, the other mutations being considered as "carried along" (and neutral as to thermostability). One notable exception is the double mutant A147E R162D: each of the two mutations was associated with a gain in residual activity.

In conclusion: the selection of more highly thermostable mutants of IFNγ was accomplished rapidly from a library of random mutants with no need for any high-throughput screening.

LEGENDS OF FIGURES

In all the figures, the sequence coding for the fusion protein $P_i$-Π is represented so that $P_i$ is upstream, which corresponds to the preferred configuration. In a particular embodiment, the opposite orientation is used, with protein Π upstream. Optionally, a sequence coding for a linker peptide of about ten amino acids is inserted between the sequence coding for $P_i$ and the sequence coding for $P_i$; for purposes of simplification the linker sequence is not shown.

FIG. 1: Example of a plasmid which can be used. Case where the genetic diversity of the library which will undergo selection is created after cloning the gene of interest (for example, by Massive Mutagenesis® technology). 1. Expression promoter in the extremophilic host; 2. Expression promoter in *E. coli;* 3. Origin of replication of the extremophilic host; 4. *E. coli* origin of replication.

FIG. 2: Example of a plasmid which can be used. Case where the library of variants of the gene of interest is directly cloned before selection by the method of the invention. Said library is created, for example, by in vitro recombination, by metagenomics technology, or by Massive Mutagenesis®. 1. Expression promoter in the extremophilic host; 2. Expression promoter in *E. coli;* 3. Origin of replication of the extremophilic host; 4. *E. coli* origin of replication.

FIG. 3: Site directed mutagenesis on the gene encoding the protein of interest, following by cloning into an expression plasmid as a fusion protein with the gene encoding the reporter protein.

FIG. 4: Cloning of the gene encoding the protein of interest as a fusion with the gene encoding the reporter protein, followed by site directed mutagenesis on the gene encoding the protein of interest, for example by Massive Mutagenesis® leading to a library of variants of the protein of interest in an expression vector such that the protein is expressed as a fusion protein with the reporter protein.

FIG. 5: Transformation of competent extremophilic bacteria with the library of variants containing the mutant gene encoding the protein of interest fused with the gene encoding the reporter protein (for example: an antibiotic resistance gene) followed by selection on solid selective medium.

FIG. 6: Transformation of competent extremophilic bacteria with the library of variants containing the mutant gene encoding the protein of interest fused with the gene encoding the reporter protein followed by selection on liquid selective medium.

FIG. 7: Negative control in liquid or solid medium. Transformation of the extremophilic bacteria with the non-mutant vector does not allow them to grow in the conditions of selection.

FIG. 8: Transformation of competent extremophilic bacteria with the library of variants containing the mutant gene encoding the protein of interest fused with the gene encoding the reporter protein followed by visual inspection of the reporter gene in solid medium.

FIG. 9: Transformation of competent bacteria with the library of variants containing the mutant gene encoding the protein of interest fused with the gene encoding the reporter protein followed by sorting by FACS (fluorescence activated cell sorter).

FIG. 10: Vectors used for selection of thermostable mutants in *T. thermophilus*. The pNCK vector contains a *T. thermophilus* origin of replication, an *E. coli* origin of replication, an ampicillin resistance gene under the control of a specific *E. coli* promoter, and a thermostable mutant of kanamycin nucleotidyltransferase, placed under the control of a promoter functional in *T. thermophilus*. Said plasmid also contains a linker peptide at its 5' end. The pNCK-vector is identical to pNCK, except that it does not contain the linker peptide at its 5' end. In the pNCK-IFNγ vector the coding frame of IFNγ has been cloned upstream of the linker peptide, taking care to preserve the reading frame.

FIG. 11: Preparation of the *T. thermophilus* system. The different vectors were transformed in *T. thermophilus* using the natural competence of this microorganism. Transformed bacteria were then spotted on a petri dish containing different concentrations of kanamycin, and incubated at different temperatures.

FIG. 12: Confirmation in *T. thermophilus* of the increased thermoresistance of certain mutants. DNA from mutants chosen in the initial selection was prepared and retransformed into *T. thermophilus*. Transformed bacteria were then plated in conditions of low stringency (70° C., 20 μg/ml kanamycin), high stringency (70° C., 40 μg/ml kanamycin), or no stringency (60° C., 20 μg/ml kanamycin). Colonies were counted in each case, and the ratios (low stringency/no stringency) and (high stringency/no stringency) were calculated.

FIG. 13: Determination of the functional activity of the mutants in comparison with wild type IFNγ. Some mutants had much lower activity than wild type IFNγ. Others showed conserved or partially conserved activity. FIG. 13A: single mutants cloned in the eukaryotic expression vector from mutations identified in the point mutants obtained in the initial selection. FIG. 13B: mutants cloned in the eukaryotic expression vector from mutations identified in the multiple mutants obtained in the initial selection.

FIG. 14: Confirmation in mammalian cells of the increased resistance of certain mutants. Activity in mammalian cells was determined before and after a treatment at 59° C. for 10 minutes. The ratio observed for wild type IFNγ was approximately 37%. Higher ratios correspond to mutants having increased thermostability. FIG. 14A: single mutants cloned in the eukaryotic expression vector from mutations identified in the point mutants obtained in the initial selection. FIG. 14B: mutants cloned in the eukaryotic expression vector from mutations identified in the multiple mutants obtained in the initial selection.

The invention claimed is:

1. A process for selecting thermostable variants of a protein of interest in thermophilic conditions comprising:
   expressing a library of fusion proteins in a thermophilic or hyper-thermophilic bacterium to generate a population of bacteria, wherein each fusion protein is a variant of a protein of interest fused to a thermostable reporter protein conferring resistance to kanamycin and whose correct expression allows the survival of the bacterium in the thermophilic conditions and in the presence of kanamycin; and
   selecting, from the population of bacteria, bacteria that survive in the thermophilic conditions and in the presence of kanamycin, thereby selecting the thermostable variants of the protein of interest.

2. The process according to claim 1, wherein the thermophilic or hyper-thermophilic bacterium is selected from the following microorganisms: *Thermus aquaticus, Thermus thermophilus, Thermotoga maritime* and *Aquifex pyrophilus*.

3. The process according to claim 1, wherein the thermostable reporter protein is a thermostable kanamycin nucleotidyltransferase.

4. The process according to claim 1, wherein the fusion protein comprises a peptide linker.

5. The process according to claim 1, wherein the protein of interest is located at the N-terminal of the thermostable reporter protein in the fusion protein.

6. The process according to claim 1, wherein the protein of interest is located at the C-terminal of the thermostable reporter protein in the fusion protein.

7. The process according to claim 1, wherein the variants of the protein of interest are generated by a mutagenesis technology selected from the group consisting of: high-throughput site directed mutagenesis, random mutagenesis, site specific mutagenesis, saturation mutagenesis, elongation mutagenesis, in vivo mutagenesis, and an in vivo or in vitro genetic recombination method, and a combination thereof.

8. The process according to claim 7, wherein the variants of the protein of interest are generated by high-throughput site directed mutagenesis technology.

9. The process according to claim 7, wherein the variants of the protein of interest are generated by in vitro circular recombination of several natural or synthetic genes encoding the protein of interest.

10. The process according to claim 1, wherein a gene encoding the protein of interest is obtained by direct cloning of nucleic acids from an environmental source.

11. The process according to claim 1, wherein the variants of the protein of interest are generated by high-throughput site directed mutagenesis technology, and each variant of the protein of interest is fused to the N-terminus of the thermostable reporter protein in the fusion protein.

12. The process according to claim 11, wherein the bacterium is *T. thermophilus*, the thermostable reporter protein is a thermostable kanamycin nucleotidyltransferase, and the fusion protein comprises a peptide linker.

13. The process according to claim 1, wherein said thermophilic conditions is a temperature of 50-110° C.

14. The process according to claim 1, wherein the process further comprises:
   a) cloning a fusion gene into a plasmid vector, the plasmid vector containing sequences necessary for its own replication in a non-thermophilic microorganism and for its expression in the thermophilic bacterium, the fusion gene comprising a gene encoding the protein of interest ($P_0$) fused to a gene encoding the thermostable kanamycin resistance protein;
   b) mutagenizing the gene encoding the protein of interest to generate a library of $P_i$ mutants;
   c) transforming the thermophilic bacterium with the library of step b); and
   d) culturing the thermophilic bacterium in the presence of kanamycin to express the library of $P_i$ mutants and selecting the thermostable variants of the protein of interest on the basis of survival of the bacteria cultured in the presence of kanamycin and in the thermophilic conditions.

15. A process for selecting mutagenized proteins having improved thermostability comprising:
   a) cloning a gene encoding a protein of interest ($P_0$) in a plasmid vector containing a gene encoding a thermostable protein conferring resistance to kanamycin (Π), said plasmid vector further comprising an *E. coli* origin of replication and an antibiotic resistance gene active in *E. coli*, and the gene encoding $P_0$ being cloned in-frame with the gene encoding Π to obtain a fusion protein ($P_0$-Π);

b) mutagenizing the gene encoding $P_0$ in *E. coli* to form a plasmid library of mutants $P_i$;

c) transforming the plasmid library obtained in step b) into a thermophilic bacterium; and d) culturing said transformed thermophilic bacteria under thermophilic conditions in the presence of kanamycin and selecting thermophilic bacteria surviving in the presence of kanamycin, wherein surviving thermophilic bacteria also express a thermostable mutagenized protein of interest.

16. The process according to claim 14, wherein said fusion gene comprises a linker between said gene encoding the protein of interest ($P_0$) and said gene encoding the thermostable kanamycin resistance protein.

17. The process according to claim 15, wherein a sequence encoding a linker peptide is inserted between the gene encoding $P_0$ and the gene encoding Π.

* * * * *